(12) United States Patent
Miller et al.

(10) Patent No.: US 9,040,033 B2
(45) Date of Patent: *May 26, 2015

(54) HYDROXYPROPYL METHYL CELLULOSE ACETATE SUCCINATE WITH ENHANCED ACETATE AND SUCCINATE SUBSTITUTION

(75) Inventors: Warren K. Miller, Bend, OR (US); David K. Lyon, Bend, OR (US); Dwayne T. Friesen, Bend, OR (US); William B. Caldwell, Bend, OR (US); David T. Vodak, Bend, OR (US); Daniel E. Dobry, Bend, OR (US)

(73) Assignee: Dow Global Technologies LLC

( * ) Notice: Subject to any disclaimer, the term of this patent is extended or adjusted under 35 U.S.C. 154(b) by 231 days.

This patent is subject to a terminal disclaimer.

(21) Appl. No.: 13/702,331

(22) PCT Filed: Jun. 13, 2011

(86) PCT No.: PCT/US2011/040222
§ 371 (c)(1),
(2), (4) Date: Jan. 8, 2013

(87) PCT Pub. No.: WO2011/159626
PCT Pub. Date: Dec. 22, 2011

(65) Prior Publication Data
US 2013/0102691 A1   Apr. 25, 2013

Related U.S. Application Data

(60) Provisional application No. 61/354,525, filed on Jun. 14, 2010.

(51) Int. Cl.
| | | |
|---|---|---|
| A61K 47/48 | (2006.01) | |
| A61K 9/14 | (2006.01) | |
| A61K 31/415 | (2006.01) | |
| A61K 31/496 | (2006.01) | |
| C08B 13/00 | (2006.01) | |
| C08L 1/32 | (2006.01) | |
| A61K 47/38 | (2006.01) | |

(Continued)

(52) U.S. Cl.
CPC ............... *A61K 47/38* (2013.01); *A61K 9/146* (2013.01); *A61K 31/415* (2013.01); *A61K 31/496* (2013.01); *C08B 13/00* (2013.01); *C08L 1/32* (2013.01)

(58) Field of Classification Search
None
See application file for complete search history.

(56) References Cited

U.S. PATENT DOCUMENTS

| | | |
|---|---|---|
| 4,226,981 A | 10/1980 | Onda et al. |
| 2007/0178152 A1 | 8/2007 | Shelton et al. |
| 2008/0262107 A1 | 10/2008 | Babcock et al. |

FOREIGN PATENT DOCUMENTS

| | | |
|---|---|---|
| EP | 1741424 A2 | 1/2007 |
| WO | 02/38126 A2 | 5/2002 |
| WO | 2005/115330 A2 | 12/2005 |

OTHER PUBLICATIONS

Japanese Pharmaceutical Excipients, 1993, pp. 182-187.

(Continued)

*Primary Examiner* — Ernst V Arnold
*Assistant Examiner* — Kyung Sook Chang

(57) ABSTRACT

Disclosed are polymers of hydroxypropyl methyl cellulose acetate succinate (HPMCAS) with unique degrees of substitution of hydroxypropoxy, methoxy, acetyl, and succinoyl groups. When used in making compositions comprising a low-solubility active agent and such polymers, the polymers provide increased aqueous concentrations and/or improved physical stability of the active agent.

16 Claims, 6 Drawing Sheets

(56) References Cited

OTHER PUBLICATIONS

Rashan, et al., Alternative liquid chromatographic method for determination of the methoxyl and 2-hydroxypropoxyl content in cellulose ether derivatives, Journal of AOAC International, vol. 86, No. 4, pp. 694-702, 2003.

Curatolo, et al., Utility of hydroxypropylmethylcellulose acetate succinate (HPMCAS) for initiation and maintenance of drug supersaturation in the GI milieu, Pharmaceutical Research, vol. 26, No. 6, Mar. 10, 2009, pp. 1419-1431.

HYDROXYPROPYL METHYL CELLULOSE ACETATE SUCCINATE WITH ENHANCED ACETATE AND SUCCINATE SUBSTITUTION

CROSS REFERENCE TO RELATED APPLICATIONS

This application is a 35 USC §371 national phase filing of PCT/US2011/040222 filed Jun. 13, 2011, which claims the benefit of U.S. Application No. 61/354,525, filed Jun. 14, 2010.

FIELD

Embodiments of hydroxypropyl methyl cellulose acetate succinate polymers, compositions comprising these polymers, methods for preparing such compositions, and methods of using such compositions are disclosed.

BACKGROUND

Pharmaceutical compositions often include polymers to achieve specific desired therapeutic effects, including for use as coating agents, as film-formers, as rate-controlling polymers for sustained or controlled release, as stabilizing agents, as suspending agents, as tablet binders, and as viscosity-increasing agents.

Hydroxypropyl methyl cellulose acetate succinate (HPMCAS) was originally developed as an enteric polymer for pharmaceutical dosage forms and for providing halation-preventing layers on photographic films. See Onda et al., U.S. Pat. No. 4,226,981. Enteric polymers are those that remain intact in the acidic environment of the stomach; dosage forms coated with such polymers protect the active agent from inactivation or degradation in the acidic environment and/or reduce irritation of the stomach by the active agent. HPMCAS is currently commercially available from Shin-Etsu Chemical Co., Ltd. (Tokyo, Japan), known by the trade name "AQOAT." Shin-Etsu manufactures three grades of AQOAT that have different combinations of substituent levels to provide enteric protection at various pH levels. The AS-LF and AS-LG grades (the "F" standing for fine and the "G" standing for granular) provide enteric protection up to a pH of 5.5. The AS-MF and AS-MG grades provide enteric protection up to a pH of 6.0, while the AS-HF and AS-HG grades provide enteric protection up to a pH of 6.8. Shin-Etsu gives the following specifications for these three grades of AQOAT polymers:

TABLE 1

| Substituent | Composition of Shin-Etsu's AQOAT Polymers (wt %) | | |
|---|---|---|---|
| | L Grades | M Grades | H Grades |
| Methoxyl Content | 20.0-24.0 | 21.0-25.0 | 22.0-26.0 |
| Hydroxypropoxyl Content | 5.0-9.0 | 5.0-9.0 | 6.0-10.0 |
| Acetyl Content | 5.0-9.0 | 7.0-11.0 | 10.0-14.0 |
| Succinoyl | 14.0-18.0 | 10.0-14.0 | 4.0-8.0 |

While pharmaceutical formulations of low-solubility active agents and HPMCAS have proven effective, the AQOAT polymers manufactured by Shin-Etsu provide only a limited selection of properties for forming such formulations.

What is desired are HPMCAS polymers designed specifically for improving the dissolved concentration of an active agent and the stability of active agents in the composition. Additionally, there is a need to adjust the properties of polymers used in pharmaceutical compositions for numerous applications, including concentration-enhancement and controlled release applications.

SUMMARY

Disclosed herein are embodiments of HPMCAS polymers with a combination of substituent levels that results in improved performance when used in pharmaceutical compositions with a low-solubility active agent. In one aspect, embodiments of HPMCAS polymers are provided, wherein the degree of substitution of methoxy groups ($DS_M$), the degree of substitution of acetyl groups ($DS_{Ac}$) and the degree of substitution of succinoyl groups ($DS_S$) on the HPMCAS are selected such that $DS_M \leq 1.45$, and the combined degree of substitution of acetyl groups and succinoyl groups, ($DS_{Ac} + DS_S) \geq 1.25$. In one embodiment, the HPMCAS polymer has a degree of substitution such that $DS_M \leq 1.45$, and $(DS_{Ac} + DS_S) \geq 1.35$. In another embodiment, the HPMCAS polymer has a degree of substitution such that $DS_M \leq 1.45$, and $(DS_{Ac} + DS_S) \geq 1.45$.

Embodiments of HPMCAS polymers are provided, wherein the degree of substitution of methoxy groups ($DS_M$), the degree of substitution of acetyl groups ($DS_{Ac}$) and the degree of substitution of succinoyl groups ($DS_S$) on the HPMCAS are selected such that $DS_M \leq 1.45$, $DS_S \geq 0.20$, $DS_{Ac} \geq 0.5$, and $(DS_{Ac} + DS_S) \geq 1.25$.

In another aspect, a pharmaceutical composition comprises an active agent, and hydroxypropyl methyl cellulose acetate succinate (HPMCAS) having a degree of substitution of methoxy groups ($DS_M$) of $\leq 1.45$, and a combined degree of substitution of acetyl groups ($DS_{Ac}$) and succinoyl groups of ($DS_S$) of $(DS_{Ac} + DS_S) \geq 1.25$. In one embodiment, the combined degree of substitution of acetyl groups ($DS_{Ac}$) and succinoyl groups of ($DS_S$) is $(DS_{Ac} + DS_S) \geq 1.35$.

In another embodiment, a pharmaceutical composition comprises an active agent, and hydroxypropyl methyl cellulose acetate succinate (HPMCAS) having a degree of substitution of methoxy groups ($DS_M$) of $\leq 1.45$, a degree of substitution of acetyl groups ($DS_{Ac}$) of $\geq 0.5$, and a degree of substitution of succinoyl groups ($DS_S$) of $\geq 0.20$.

In another embodiment, the HPMCAS has a degree of substitution such that $1.25 \leq (DS_{Ac} + DS_S) \leq 1.9$. In still another embodiment, the HPMCAS has a degree of substitution such that $1.5 \leq (DS_{Ac} + DS_S) \leq 1.7$. In yet another embodiment, the HPMCAS has a degree of substitution such that $DS_{Ac} \geq 0.5$, $DS_S \geq 0.20$, and $1.25 \leq (DS_{Ac} + DS_S) \leq 1.9$.

In another embodiment, a pharmaceutical composition comprises an active agent, and HPMCAS having a degree of substitution of methoxy groups ($DS_M$) of $\leq 1.45$, a combined degree of substitution of acetyl groups ($DS_{Ac}$) and succinoyl groups of ($DS_S$) of $(DS_{Ac} + DS_S) \geq 1.25$, $DS_{Ac} \leq 1.2$, and $DS_S \leq 0.9$.

In another embodiment, a pharmaceutical composition comprises an active agent and hydroxypropyl methyl cellulose acetate succinate (HPMCAS) having a degree of substitution of methoxy groups ($DS_M$) of $\leq 1.45$, a combined degree of substitution of acetyl groups ($DS_{Ac}$) and succinoyl groups ($DS_S$) of $\geq 1.25$, and a ratio of acetyl groups to succinoyl groups between 0.8 and 6.5. In another embodiment, the ratio of acetyl groups to succinoyl groups is between 1.0 and 6.0. In still another embodiment, the ratio of acetyl groups to succinoyl groups is between 1.2 and 5.6. In one embodiment, the HPMCAS has a degree of substitution such that $1.0 \leq DS_{Ac} \leq 1.5$, and $0.20 \leq DS_S \leq 0.7$.

In one embodiment, the composition is in the form of a solid amorphous dispersion of an active agent and the HPMCAS, wherein at least 90 wt % of the active agent in the dispersion is non-crystalline.

In one embodiment, a method comprises increasing the efficacy of an active agent by providing a polymer, wherein the polymer is hydroxypropyl methyl cellulose acetate succinate (HPMCAS) having a degree of substitution of methoxy groups ($DS_M$) of ≤1.45, a degree of substitution of acetyl groups ($DS_{Ac}$) of ≥0.5, and a degree of substitution of succinoyl groups ($DS_S$) of ≥0.20, and combining the polymer with an active agent to form a solid amorphous dispersion comprising 5-95 wt % active agent, wherein the solid amorphous dispersion is capable of increasing aqueous solubility of the active agent at least 1.25-fold compared to aqueous solubility of the active agent without the polymer.

In another embodiment, the method comprises increasing the efficacy of an active agent by providing a polymer, wherein the polymer is hydroxypropyl methyl cellulose acetate succinate (HPMCAS) having a degree of substitution of methoxy groups ($DS_M$) of ≤1.45, a degree of substitution of acetyl groups ($DS_{Ac}$) of ≥0.5, and a degree of substitution of succinoyl groups ($DS_S$) of ≥0.20, and combining the polymer with an active agent to produce a pharmaceutical composition, wherein the pharmaceutical composition is capable of increasing aqueous solubility of the active agent at least 1.25-fold compared to the active agent without the polymer.

In another embodiment, the method comprises increasing the efficacy of an active agent by providing a polymer, wherein the polymer is hydroxypropyl methyl cellulose acetate succinate (HPMCAS) having a degree of substitution of methoxy groups ($DS_M$) of ≤1.45, a degree of substitution of acetyl groups ($DS_{Ac}$) of ≥0.5, and a degree of substitution of succinoyl groups ($DS_S$) of ≥0.20, and combining the polymer with an active agent to form a pharmaceutical composition having an active agent to polymer ratio from 0.05 to 20; and orally administering the pharmaceutical composition to a subject, wherein the pharmaceutical composition is capable of increasing active agent concentration in the subject's blood at least 1.25-fold compared to administering the active agent without the polymer.

In another embodiment, the method comprises increasing the efficacy of an active agent by administering a polymer to a subject, wherein the polymer is hydroxypropyl methyl cellulose acetate succinate (HPMCAS) having a degree of substitution of methoxy groups ($DS_M$) of ≤1.45, a degree of substitution of acetyl groups ($DS_{Ac}$) of ≥0.5, and a degree of substitution of succinoyl groups ($DS_S$) of ≥0.20, and administering an active agent to the subject simultaneously with the polymer or less than 60 minutes after administering the polymer, wherein administering the polymer and active agent to the subject is capable of increasing active agent concentration in the subject's blood at least 1.25-fold compared to administering the active agent without the polymer.

The disclosed embodiments provide one or more of the following advantages. The HPMCAS polymers have a combination of substituent degrees of substitution that enhances the concentration of dissolved active agent for low-solubility active agents in a use environment. When used to form solid amorphous dispersions of low-solubility active agents, and in particular, hydrophobic active agents, the polymers allow higher amounts of active agent in the dispersion and still remain homogeneous upon storage, while providing enhanced concentrations of dissolved active agent in a use environment. When used in combination with active agents that are prone to rapid crystallization from supersaturated aqueous solutions, some embodiments of the disclosed polymers are particularly effective at sustaining high active agent concentrations and thereby enhancing absorption of active agent in vivo. Additionally, dispersions of low-solubility active agents and the inventive polymers may provide improved physical stability when compared to dispersions made with commercial grades of HPMCAS.

The foregoing and other objects, features, and advantages of the disclosed embodiments will become more apparent from the following detailed description, which proceeds with reference to the accompanying figures.

DETAILED DESCRIPTION

Figure 1:
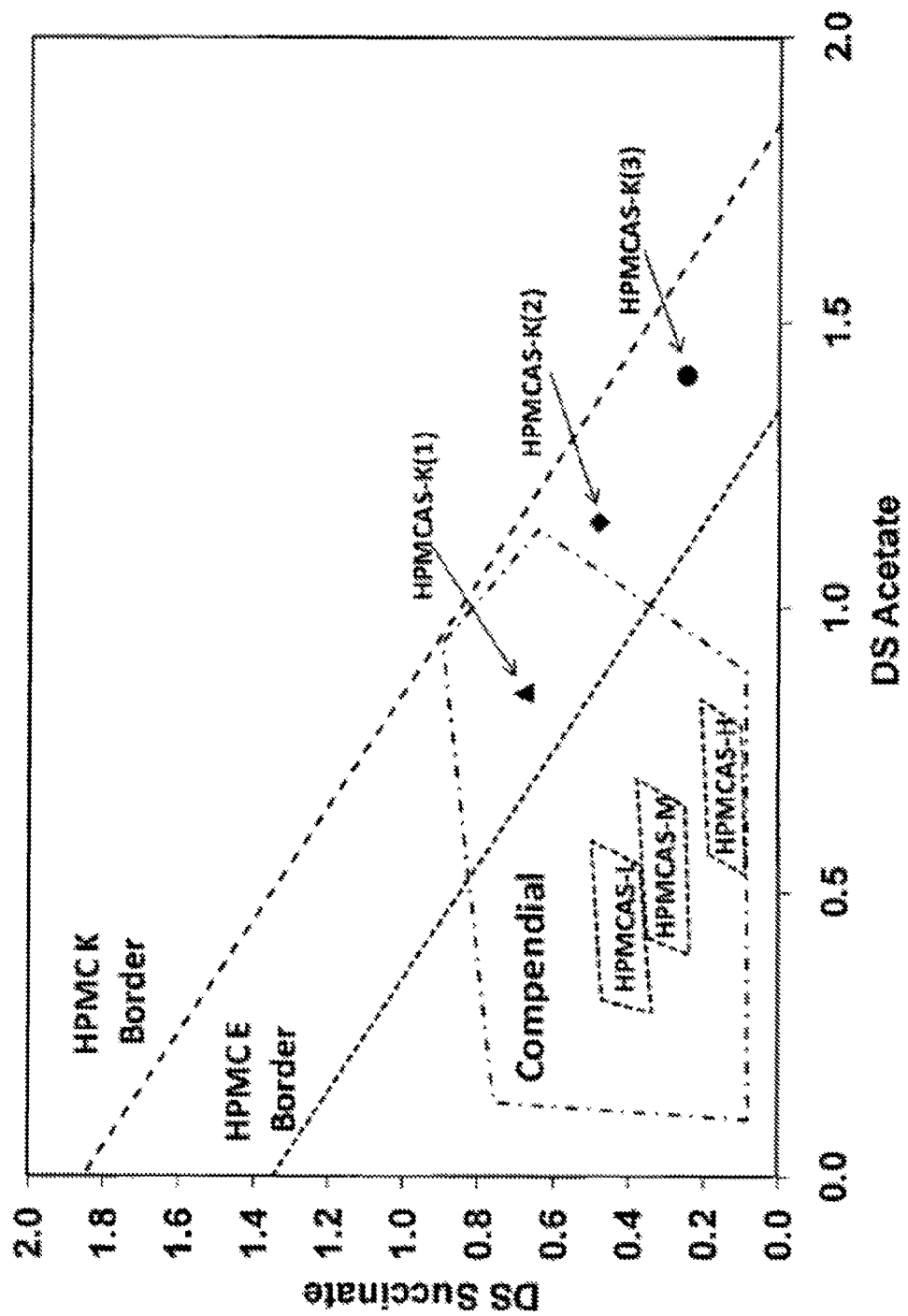
FIG. 1 is a graph of degree of succinate substitution versus degree of acetate substitution for several embodiments of HPMCAS polymers.

Hydroxypropyl methyl cellulose acetate succinate (HPMCAS) polymers with a unique combination of substitution levels, and methods for making such polymers are provided. Also provided are compositions including the HPMCAS polymers and active agents, along with methods of preparing and using such compositions.

Unless otherwise indicated, all numbers expressing quantities of ingredients, properties such as molecular weight, percentages, and so forth, as used in the specification or claims are to be understood as being modified by the term "about." Unless otherwise indicated, non-numerical properties such as amorphous, crystalline, homogeneous, and so forth as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

I. TERMS AND ABBREVIATIONS

The following explanations of terms and abbreviations are provided to better describe the present disclosure and to guide those of ordinary skill in the art in the practice of the present disclosure. As used in this application and in the claims, the singular forms "a," "an," and "the" include the plural forms unless the context clearly dictates otherwise. Additionally, the terms "includes" or "having" mean "comprises." The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

An active agent, as used herein, is a drug, medicament, pharmaceutical, therapeutic agent, nutraceutical, or other compound that may be administered to the subject. In one embodiment, the active agent is a "small molecule," generally having a molecular weight of 2000 daltons or less.

Amorphous means non-crystalline, having no or substantially no molecular lattice structure. Liquids are amorphous. Some solids or semisolids, such as glasses, rubber, and some polymers, are also amorphous. Amorphous solids and semisolids lack a definite crystalline structure and a well-defined melting point.

Cellulose is a naturally occurring polysaccharide of about 70 to more than 10,000 β(1→4) linked D-glucose units in a linear chain. Cellulose has the general formula $(C_6H_{10}O_5)_n$ and the following general repeat unit:

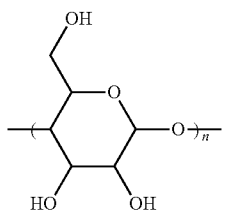

Degree of substitution (DS) means the average number of a substituent or group that is substituted per repeat unit in a polymer chain. For example, if there is an average of two acetyl groups per saccharide repeat of cellulose, the degree of substitution, $DS_{Ac}$, is 2.

A dispersion is a system in which particles are distributed throughout a different composition. A solid dispersion is a system in which particles of at least one solid component are dispersed throughout another solid component. A molecular dispersion is a system in which at least one component is homogeneously or substantially homogeneously dispersed on a molecular level throughout another component. A molecular dispersion is also known as a solid solution.

An excipient is a physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition.

The glass transition temperature, $T_g$, is the temperature at which an amorphous solid, such as glass or a polymer, becomes brittle or strong on cooling, or soft or pliable on heating. $T_g$ can be determined, for example, by differential scanning calorimetry (DSC). DSC measures the difference in the amount of heat required to raise the temperature of a sample and a reference as a function of temperature. During a phase transition, such as a change from an amorphous state to a crystalline state, the amount of heat required changes. For a solid that has virtually no crystalline components, a single glass transition temperature indicates that the solid is a molecular dispersion.

Molecular weight is the sum of the atomic weights of the atoms in a molecule. As used herein with respect to polymers, the terms molecular weight, average molecular weight, mean molecular weight, and apparent molecular weight refer to the arithmetic mean of the molecular weights of individual macromolecules as measured by size-exclusion chromatography (SEC) as follows. A sample of the polymer is dissolved at a concentration of 2 mg/mL in a mobile phase, consisting of 40:60 (v:v) acetonitrile:mobile-phase buffer (consisting of 6 mg/mL sodium dihydrogen phosphate and 8.5 mg/mL sodium nitrate dissolved in water), adjusted to pH 8 using 10 M NaOH. A 100 μL sample is tested by SEC using a TSK-GEL® GMPW$_{XL}$ 300×7.8 mm column (Tosoh Bioscience), operating at 0.5 mL/min mobile phase at about 40° C. Samples are detected using a multi-angle laser light scattering (MALLS) detector and a differential refractive index (RI) detector. The molecular weight measured by this method is apparent because it is specific to the solvent system used in this analysis. The molecular weight distribution is characterized by the weight-averaged molecular weight ($M_W$) and the polydispersity (PD) which is the ratio of weight-averaged over the number-averaged molecular weights.

A monosaccharide is a basic unit of a polysaccharide. Monosaccharides are simple sugars with the basic chemical formula $C_x(H_2O)_y$, where x and y are integers. Typically, y=x or y=x−1. Many monosaccharides are pentoses (x=5) or hexoses (x=6). Examples of monosaccharides include arabinose, fructose, galactose, glucose, ribose, and xylose, among others.

The term particle is commonly understood to mean a very small or tiny mass of material. With respect to crystalline materials, particle typically refers to an individual crystal.

Pharmaceutically acceptable refers to a substance that can be taken into a subject without significant adverse toxicological effects on the subject. The term "pharmaceutically acceptable form" means any pharmaceutically acceptable derivative or variation, such as stereoisomers, stereoisomer mixtures, enantiomers, solvates, hydrates, isomorphs, polymorphs, pseudomorphs, neutral forms, salt forms, and prodrug agents.

A polymer is a molecule of repeating structural units (e.g., monomers) formed via a chemical reaction, i.e., polymerization.

A polysaccharide is a polymer of monosaccharides linked together by glycosidic bonds. Common examples include hemicellulose, cellulose, starch, and dextran.

A powder is a composition comprising solid particles that are relatively free flowing from one another and capable of being dispersed.

A solid solution is formed when at least one solid component is molecularly dispersed within another solid component, resulting in a homogeneous or substantially homogeneous solid material. A solid solution may be formed, for example, by completely or substantially completely dissolving two solid components in a liquid solvent and then removing the liquid solvent to produce the solid solution. A solid solution is also known as a molecular dispersion.

Soluble means capable of becoming molecularly or ionically dispersed in a solvent to form a solution.

A solution is a homogeneous or substantially homogeneous mixture composed of two or more substances.

A suspension is a heterogeneous mixture in which particles are dispersed substantially uniformly in a liquid or gaseous medium. Without agitation, the particles tend to separate over time from the liquid or gaseous medium.

II. HYDROXYPROPYL METHYL CELLULOSE ACETATE SUCCINATE

Hydroxypropyl methyl cellulose acetate succinate (HPMCAS) is a substituted cellulosic polymer. By "substituted cellulosic polymer" is meant a cellulose polymer that has been modified by reaction of at least a portion of the hydroxyl groups on the saccharide repeat units with a compound to form an ester-linked or an ether-linked substituent. HPMCAS contains 2-hydroxypropoxy groups (—OCH$_2$CH(CH$_3$)OH, hereinafter referred to as hydroxypropoxy groups) ether linked to the saccharide repeat unit by substitution on any hydroxyl group present on the repeat unit, or linked to a hydroxyl group on another hydroxypropoxy group. HPMCAS also contains methoxy groups (—OCH$_3$), ether linked to the saccharide repeat unit by substitution on any hydroxyl group present on the repeat unit. HPMCAS also contains acetyl groups (—COCH$_3$) ester linked to the saccharide repeat unit by substitution on any hydroxyl group present on the repeat unit. HPMCAS also contains succinoyl groups (—COCH$_2$CH$_2$COOH) ester linked to the saccharide repeat unit by substitution on any hydroxyl group present on the repeat unit.

Thus, as used herein and in the claims, by "HPMCAS" is meant a cellulosic polymer comprising 2-hydroxypropoxy groups (—OCH$_2$CH(CH$_3$)OH), methoxy groups (—OCH$_3$), acetyl groups (—COCH$_3$), and succinoyl groups (—COCH$_2$CH$_2$COOH). Other substituents can be included on the polymer in small amounts, provided they do not materially affect the performance and properties of the HPMCAS.

The amount of any one substituent on the polymer is characterized by its degree of substitution on the polymer. By "degree of substitution" of a substituent or group on the polymer is meant the average number of that substituent that is substituted on each saccharide repeat unit on the cellulose chain. The substituent may be attached directly to the saccharide repeat unit by substitution for any of the three hydroxyls on the saccharide repeat unit, or they may be attached through a hydroxypropoxy substituent, the hydroxypropoxy substituent being attached to the saccharide repeat unit by substitution for any of the three hydroxyls on the saccharide repeat unit. For example, an acetyl substituent may be attached to a hydroxyl group on the saccharide repeat unit or to the hydroxyl group on a hydroxypropoxy substituent as follows:

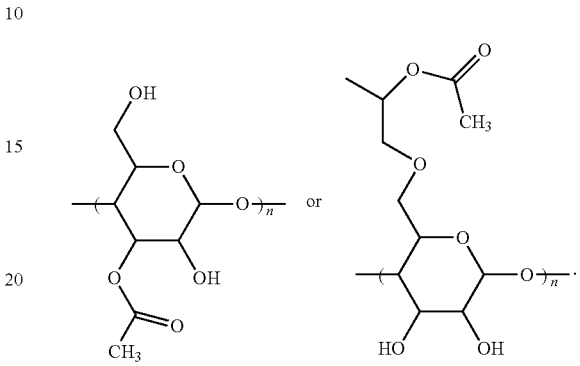

DS represents the average number of a given substituent on the saccharide repeat unit. Thus, if on average 1.3 hydroxyls on the saccharide repeat unit are substituted with a methoxy group, DS$_M$ would be 1.3. As another example, if two of the three hydroxyls on the saccharide repeat unit have been substituted with a methoxy group, the DS$_M$ would be 2.0. In another example, if one of the three hydroxyls on the saccharide repeat unit have been substituted with an hydroxypropoxy group, one of the remaining two hydroxyls on the saccharide repeat unit have been substituted with a methoxy group, and the hydroxyl on the hydroxypropoxy group has been substituted with a methoxy group, the DS$_{HP}$ would be 1.0 and the DS$_M$ would be 2.0. Suitable methods to vary the degree of substitution of various substituents on the polymer, and methods for forming pharmaceutical compositions, are described in more detail below.

The prior art HPMCAS polymers obtained from Shin-Etsu have the following typical combination of substituent levels, where the ranges given are for a number of different lots of polymers obtained from Shin-Etsu, as indicated in the table:

TABLE 2

| | | L Grades | | M Grades | | H Grades | |
|---|---|---|---|---|---|---|---|
| Item | Substituent | Range* | Average (of 12 lots) | Range* | Average (of 28 lots) | Range* | Average (of 17 lots) |
| Manufacturer's Certificate of Analysis (wt %) | Methoxyl | 21.7-22.5 | 22.1 ± 0.3 | 22.7-23.6 | 23.1 ± 0.2 | 23.2-24.1 | 23.7 ± 0.3 |
| | Hydroxypropoxyl | 6.8-7.1 | 7.0 ± 0.1 | 7.0-7.9 | 7.3 ± 0.2 | 7.1-7.8 | 7.5 ± 0.2 |
| | Acetyl | 7.2-8.1 | 7.7 ± 0.3 | 8.7-10.8 | 9.3 ± 0.4 | 11.0-12.2 | 11.5 ± 0.3 |
| | Succinoyl | 15.1-16.5 | 15.5 ± 0.4 | 10.8-11.5 | 11.2 ± 0.2 | 5.3-7.6 | 6.5 ± 0.7 |
| Calculated Degree of Substitution** | [1]DS$_M$ | 1.84-1.91 | 1.87 ± 0.03 | 1.85-1.94 | 1.89 ± 0.02 | 1.84-1.92 | 1.88 ± 0.02 |
| | [2]DS$_{HP}$ | 0.24-0.25 | 0.25 ± 0.01 | 0.24-0.27 | 0.25 ± 0.01 | 0.23-0.26 | 0.24 ± 0.01 |
| | [3]DS$_{Ac}$ | 0.44-0.49 | 0.47 ± 0.02 | 0.51-0.65 | 0.55 ± 0.03 | 0.62-0.70 | 0.66 ± 0.02 |
| | [4]DS$_S$ | 0.39-0.43 | 0.40 ± 0.01 | 0.27-0.29 | 0.28 ± 0.01 | 0.13-0.19 | 0.16 ± 0.02 |
| | DS$_M$ + DS$_{Ac}$ + DS$_S$ | 2.70-2.80 | 2.75 ± 0.03 | 2.65-2.87 | 2.71 ± 0.03 | 2.63-2.73 | 2.70 ± 0.03 |
| | DS$_{Ac}$ + DS$_S$ | 0.85-0.89 | 0.88 ± 0.01 | 0.80-0.93 | 0.83 ± 0.03 | 0.77-0.84 | 0.81 ± 0.02 |

*Range of several lots of polymer for each grade (the number of lots is indicated under "Average").
**Degree of substitution calculated as described herein.
[1]DS$_M$ = degree of substitution of methoxy groups
[2]DS$_{HP}$ = degree of substitution of hydroxypropoxy groups
[3]DS$_{Ac}$ = degree of substitution of acetyl groups
[4]DS$_S$ = degree of substitution of succinoyl groups The inventors found that, by varying the combination of substituent levels on the HPMCAS, novel grades of HPMCAS can be prepared in which some low-solubility active agents, particularly those that are hydrophobic, have even higher solubility in the dispersion. This results in physically stable solid amorphous dispersions with high active agent loadings. Further work with these novel grades of HPMCAS showed that dispersions or mixtures with solubility-improved forms of certain active agents provide concentration enhancement and improve inhibition of crystallization or precipitation.

Specifically, the inventors have found that some embodiments of HPMCAS polymers with improved performance and/or utility have a lower $DS_M$, a higher $DS_{Ac}$, and/or a higher total substitution of acetyl and succinoyl groups (that is, $DS_{Ac}+DS_S$) than the commercial grades of HPMCAS. A high $DS_{Ac}$ is desirable because it provides more hydrophobic groups that lead to an increased solubility of low-solubility active agents in the polymer. At the same time, the degree of substitution of succinoyl groups desirably is of at least a sufficient value as to render the polymer aqueous soluble or dispersible at a pH of 5 to 8.

HPMCAS is synthesized from hydroxypropyl methyl cellulose (HPMC). The disclosed HPMCAS polymers preferably have a methoxy degree of substitution that is less than or equal to 1.45. Surprisingly, it was determined that HPMCAS with this degree of substitution of methoxy groups has superior utility for pharmaceutical formulations. Without being bound to any particular theory, it is believed that a low $DS_M$ is desirable because it provides more available sites for substitution with acetyl and succinoyl groups. Compared to HPMC with a $DS_M$ of 1.9 (HPMC grade E, or "HPMC-E"), HPMC with a $DS_M$ of 1.4 ("HPMC-K") has approximately 0.5 more sites per saccharide repeat unit that are available for substitution by acetate and/or succinate substituents. Decreasing the $DS_M$ is a result-effective variable that has not previously been recognized in the preparation of HPMCAS polymers and their utility in pharmaceutical compositions comprising low-solubility active agents.

In one embodiment, the HPMCAS polymers have a $DS_M \leq 1.45$ and a $(DS_{Ac}+DS_S) \geq 1.25$. In another embodiment, the HPMCAS polymers have a $DS_M \leq 1.45$ and a $(DS_{Ac}+DS_S) \geq 1.35$. In still another embodiment, the HPMCAS polymers have a $DS_M \leq 1.45$ and a $(DS_{Ac}+DS_S) \geq 1.45$.

The $DS_{HP}$ preferably ranges from 0.10 to 0.35. The $DS_{HP}$ may also range from 0.15 to 0.30. Surprisingly, it was determined that HPMCAS with this degree of substitution of hydroxypropoxy groups has superior utility for pharmaceutical formulations.

Some embodiments of the disclosed HPMCAS polymers have a $DS_{Ac}$ of at least 0.5. In other embodiments, $DS_{Ac}$ is 0.8-1.5. In still other embodiments, $DS_{Ac}$ is 1.0-1.5. Surprisingly, it was determined that HPMCAS polymers with a high $DS_{Ac}$ have superior performance and utility for pharmaceutical formulations. HPMCAS polymers prepared from HPMC grade E typically have a $DS_{Ac}$ of 0.4-0.7. The increased acetate substitution in the disclosed HPMCAS polymers leads to increased solubility of low-solubility active agents in the polymer, thus broadening the number of potential active agents that can be successfully administered in pharmaceutical compositions comprising HPMCAS. Potential active agents that were previously discarded from consideration due to poor solubility in the conventional polymers may have sufficient solubility and hence utility when combined with the disclosed HPMCAS polymers in pharmaceutical compositions.

Certain embodiments of the disclosed HPMCAS polymers have a $DS_S$ of at least 0.20, such as 0.20-0.7. In one embodiment, $DS_S$ is at least 0.35, such as 0.35-0.7. Surprisingly, it was determined that HPMCAS polymers with this degree of substitution of succinoyl groups have improved performance and utility for pharmaceutical formulations. Increased substitution by succinoyl groups enables the pharmaceutical formulations to sustain the enhanced drug concentration for longer times compared to conventional HPMCAS polymers.

In particular embodiments, the combined degree of substitution of acetyl and succinoyl groups on the HPMCAS is greater than a minimum value. In one embodiment, $(DS_{Ac}+DS_S) \geq 1.25$; in another embodiment, $1.25 \leq (DS_{Ac}+DS_S) \leq 1.9$; in yet another embodiment, $1.5 \leq (DS_{Ac}+DS_S) \leq 1.7$. The combined $DS_{Ac}+DS_S$ substitution in HPMCAS polymers synthesized from HPMC grade K is approximately twice that found in HPMCAS polymers synthesized from HPMC grade E, which have a combined $(DS_{Ac}+DS_S)$ substitution of 0.8-0.9. The inventors have found that HPMCAS with this combined degree of substitution of acetyl and succinoyl groups provides unexpectedly superior results in pharmaceutical formulations. The increase in both acetate and succinate groups has a synergistic effect on the polymer properties. In particular, the high combined degree of substitution increases the amphiphilic nature of the HPMCAS polymers and enables the polymers to exhibit increased micellar behavior in aqueous solutions. Additionally, the increased acetate substitution allows increased solubility of low-solubility active agents in the SDD, while the increased succinate substitution increases solubility of the polymer in aqueous solution. The increased degrees of substitution of both acetyl and succinoyl groups provides the disclosed HPMCAS polymers with superior properties and versatility for use in preparing pharmaceutical compositions as compared to HPMCAS polymers prepared from HPMC grade E.

In one embodiment, the HPMCAS has a degree of substitution such that $1.0 \leq DS_{Ac} \leq 1.5$, and $0.20 \leq DS_S \leq 0.7$. In another embodiment, the HPMCAS has a degree of substitution of methoxy groups $(DS_M)$ of $\leq 1.45$, and a combined degree of substitution of acetyl groups $(DS_{Ac})$ and succinoyl groups of $(DS_S)$ of $(DS_{Ac}+DS_S) \geq 1.25$, $DS_{Ac} \leq 1.2$, and $DS_S \leq 0.9$.

In another embodiment, the HPMCAS has a degree of substitution of methoxy groups $(DS_M)$ of $\leq 1.45$, a combined degree of substitution of acetyl groups $(DS_{Ac})$ and succinoyl groups $(DS_S)$ of $\geq 1.25$, and a ratio of acetyl groups to succinoyl groups between 0.8 and 6.5. In another embodiment, the ratio of acetyl groups to succinoyl groups is between 1.0 and 6.0. In still another embodiment, the ratio of acetyl groups to succinoyl groups is between 1.2 and 5.6.

FIG. 1 illustrates the HPMC-K and HPMC-E borders, i.e., the maximum combined $DS_{Ac}+DS_S$ possible based upon the number of available sites for substitution. FIG. 1 also shows $DS_S$ and $DS_{Ac}$ for three embodiments of the disclosed HPMCAS polymers (HPMCAS-K(1), HPMCAS-K(2), HPMCAS-K(3)) and three commercially available HPMCAS polymers from Shin-Etsu (L, M, H). As the graph clearly shows, for any given $DS_{Ac}$, the disclosed polymers can have a much higher $DS_S$ than corresponding polymers prepared from the Shin-Etsu polymer, HPMC-E. Similarly, for any given $DS_S$, the disclosed polymers have a much higher $DS_{Ac}$.

The inventors have discovered that pharmaceutical compositions of active agents made with polymers that meet these criteria provide concentration enhancement or improved physical stability or both relative to control compositions as outlined herein.

III. SYNTHESIS OF HPMCAS

Methods for synthesis of HPMCAS are well known in the art. See, for example, Onda et al., U.S. Pat. No. 4,226,981 and

*Comprehensive Cellulose Chemistry* by Klemm et al. (1998; see pages 164-197 and 207-249), the teachings of which are incorporated herein by reference. HPMCAS may be synthesized by treating o-(hydroxypropyl)-o-methylcellulose (i.e., HPMC) with acetic anhydride and succinic anhydride, as disclosed in, for example, U.S. Published Patent Application No. 2008/0262107, which is incorporated herein by reference. Sources for HPMC include Dow (Midland, Mich.), Shin-Etsu (Tokyo, Japan), Ashland Chemical (Columbus, Ohio), Aqualon (Wilmington, Del.), and Colorcon (West Point, Pa.). A variety of HPMC starting materials are available, with various degrees of substitution of hydroxypropoxy and methoxy substituents. One skilled in the art will realize that the choice of HPMC starting material will have an influence on the solubility parameter and other properties of the polymer generated therefrom. In a preferred embodiment, the HPMC has a $DS_M$ less than or equal to 1.45, a $DS_{HP}$ ranging from 0.18 to 0.35, and an apparent viscosity of 2.4 to 3.6 cp. Examples of such polymers include the METHOCEL® K3 Premium LV grade ("HPMC-K") available from Dow (Midland, Mich.). Alternatively, the HPMC may be synthesized from cellulose using methods well known in the art. For example, cellulose may be treated with sodium hydroxide to produce swollen alkali cellulose, and then treated with chloromethane and propylene oxide to produce HPMC. See *Comprehensive Cellulose Chemistry* by Klemm et al. (1998). The HPMC starting material preferably has a molecular weight ranging from 600 to 60,000 daltons, preferably 3,000 to 50,000 daltons, more preferably 6,000 to 30,000 daltons.

The degree of substitution of hydroxypropoxy, methoxy, acetyl, and succinoyl groups on the polymer can be determined from the weight percent of the substituent on the polymer, which can be determined using methods well known in the art. See, for example, U.S. Pat. No. 4,226,981 and *Japanese Pharmaceutical Excipients* (1993, pages 182-187), the disclosures of which are herein incorporated by reference. The weight percentage of substituents is the industrially accepted method for characterization of the amounts of substituents on the polymers. However, the inventors have discovered that the degree of substitution of the substituents on the cellulose backbone provides a more meaningful parameter for determining the effectiveness of a given grade of polymer for use in pharmaceutical compositions. In particular, when the degree of substitution of one component of the polymer is changed, the degrees of substitution of the other components stay the same. However, when weight percent is used, a change in the weight percentage of one component results in a change in the weight percentage of all components of the polymer, even if the degree of substitution is not changed. This is because the weight percent is based on the total weight of the cellulose repeat unit, including all substituents.

By convention, the weight percentage of hydroxypropoxy groups is reported based on the mass of hydroxypropoxy groups (i.e., —OCH$_2$CH(CH$_3$)OH) attached to the saccharide group, the weight percentage of methoxy groups is reported based on the mass of methoxy groups (i.e., —OCH$_3$), the weight percentage of acetyl groups is reported based the mass of acetyl groups (i.e., —COCH$_3$), and the weight percentage of succinoyl groups is reported based on the mass of succinoyl groups (i.e., —COCH$_2$CH$_2$COOH). This convention is used herein when discussing weight percentages of substituents.

Rashan et al. (*Journal of AOAC International*, Vol. 86, No. 4, p. 694-702, 2003) provide a procedure for determining the weight percentage of hydroxypropoxy and methoxy groups on a polymer as follows. A 60-70 mg sample of the polymer is weighed into a vial. To this same vial is added 70-130 mg of adipic acid and a 2-mL portion of 57 wt % hydriodic acid in water. A 2-mL portion of o-xylene is then added into the vial and the vial is capped and weighed. The vial is then heated to 150° C. and periodically shaken. After 1 hour of heating, the vial is allowed to cool to ambient temperature, and the vial is weighed again to assure a weight loss of less than 10 mg. The two phases are allowed to separate, and 1.5 mL of the top o-xylene layer is removed using a pipet and placed into a small glass vial (without disturbing the bottom aqueous layer). Next, 1-mL of the o-xylene layer that was removed is accurately measured into a 10-mL volumetric flask, diluted to volume with methanol, and mixed well. This is labeled as the Test Sample.

Standard solutions are prepared as follows. Approximately 2 mL o-xylene is placed into a 10-mL volumetric flask. Approximately 200 µL of iodomethane is then added to the flask and the weight of iodomethane added is recorded. Approximately 34 µL of 2-iodopropane is then added to the flask and the weight of iodopropane added is recorded. The contents of the flask are then brought to volume with o-xylene and the flask well mixed.

Next, 80-90 mg adipic acid is added to an 8 mL vial. To this same vial is added 2 mL hydriodic acid (57 wt % in water) and the vial shaken. The layers are allowed to separate, and 1.5 mL of the top o-xylene layer is removed using a pipet and placed in a small glass vial. Next, 1-mL of the o-xylene layer that was removed is accurately measured into a 10-mL volumetric flask, diluted to volume with methanol, and mixed well. This is labeled as the Standard.

The Test Sample and Standard are analyzed by high-performance liquid chromatography (HPLC) as follows. Mobile Phase A is 90/10 v/v water/methanol and Mobile Phase B is 15/85 v/v water/methanol. A 10-µL volume of the Test Sample or Standard is injected in to an HPLC. The HPLC is equipped with an AQUASIL® column (5 µm, C$_{18}$ 125 Å, 150×4.60 mm). The flow rate is 1.0 mL/min with the following gradient profile: at 0.00 min, 70% Mobile Phase A, 30% Mobile Phase B; at 8.00 min, 40% A, 60% B; at 10.00 min, 15% A, 85% B; at 17 min, 15% A, 85% B; and at 17.01 min, 70% A, 30% B. Detection is by UV at a wavelength of 254 nm.

To calculate the amount of hydroxypropoxy and methoxy on the polymer sample, the standard response factor (RF$_i$) for species i based on the results with the Standard is calculated from the following equation:

$$RF_i = \frac{A_{std,i} * DF_{std,i} * V_{std,i}}{W_{std,i} * PF_i}$$

where $A_{Std,i}$ is the peak area obtained for species i, $DF_{Std,i}$ is the dilution factor for species i, $_{Std,i}$ is the volume of o-xylene used for preparing the standard, $W_{Std,i}$ is the weight, in mg, of species i used for preparing the standard, and PF$_i$ is the purity factor for species i. The response factor is calculated for both iodomethane and for 2-iodopropane.

The amount of species i in the Test Sample is calculated from the following equation:

$$W_i = \frac{A_i * DF_i * V_i}{RF_i}$$

where the variables have the same definitions as above except that the values are for the Test Solution rather than for the Standard. The amounts of both iodomethane and 2-iodopropane are calculated in this manner.

The amount (wt %) of methoxy groups (—OCH$_3$) in the polymer is then calculated by the following equation:

$$\text{Methoxy (wt \%)} = 100 \times \frac{31.03}{141.94} \times \frac{W_{iodomethane}}{\text{weight of polymer}}$$

where $W_{iodomethane}$ is given by the above equation.

Similarly, the amount (wt %) of hydroxypropoxy groups (—OCH$_2$CH(CH$_3$)OH) in the polymer is calculated by the following equation:

$$\text{Hydroxypropoxy (wt \%)} = 100 \times \frac{75.09}{169.99} \times \frac{W_{2\text{-}iodopropane}}{\text{weight of polymer}}$$

where $W_{2\text{-}iodopropane}$ is given by the above equation.

Another procedure for determining the weight percentage of hydroxypropoxy and methoxy groups on a polymer is set forth in *Japanese Pharmaceutical Excipients*, pages 182-187 (1993).

The weight percentage of acetyl and succinoyl groups in HPMCAS may be determined by a high-performance liquid chromatography (HPLC) procedure as follows. First, a 12.4-mg sample of the polymer is placed into a glass vial. To the vial, 4 mL of 1.0 N NaOH is added to hydrolyze the polymer by stirring for 4 hours using a magnetic stirrer. Then 4 mL of 1.2 M H$_3$PO$_4$ solution is added to lower the solution pH to less than 3. The sample solution vial is inverted several times to ensure complete mixing. The sample solution is then filtered through a 0.22-μm syringe filter into an HPLC vial prior to analysis.

As a control, a non-hydrolyzed polymer sample is prepared by first weighing out 102.4 mg of the polymer into a vial. To the vial, 4 mL of 20 mM KH$_2$PO$_4$ solution at pH 7.50 (adjusted for pH by drop wise adding a 1.0 N sodium hydroxide solution) are added to dissolve the polymer by stirring for 2 hours using a magnetic stirrer. Then, 4 mL of 25 mM H$_3$PO$_4$ solution is added to precipitate the polymer out of solution. The vial is inverted several times to ensure complete mixing. The control solution is then filtered through a 0.22-μm syringe filter into an HPLC vial prior to analysis.

The sample solution and control solution are analyzed by HPLC using a Phenomenex AQUA® 5μ C18 column (without a guard column) with sample detection at 215 nm and a sample size of 10 μL. The mobile phase is 20 mM KH$_2$PO$_4$ at pH 2.8 at a flow rate of 1.00 mL/min at ambient temperature.

A series of standards of acetic acid and succinic acid are prepared for calibration. From the HPLC analysis, the concentration of acetic acid and succinic acid in the sample solution and control solution are determined.

The acetyl and succinoyl contents of the HPMCAS are calculated from the measured acetic and succinic acids in the hydrolyzed sample solution and the measured free acetic and succinic acids in the non-hydrolyzed control solutions. The formulae used for calculations are as follows:

$$\text{Free Acetic Acid (wt \%)} = 100 \times \frac{[\text{Acetic Acid}]_{free}(\text{mg/mL})}{[\text{Polymer}]_{free}(\text{mg/mL})}, \text{ and}$$

$$\text{FreeSuccinic Acid (wt \%)} = 100 \times \frac{[\text{Succinic Acid}]_{free}(\text{mg/mL})}{[\text{Polymer}]_{free}(\text{mg/mL})},$$

where [Acetic Acid]$_{free}$ and [Succinic Acid]$_{free}$ are the concentrations of free acetic and free succinic acids in the non-hydrolyzed control solutions, respectively; and [Polymer]$_{free}$ is the concentration of the initially added HPMCAS in the non-hydrolyzed control solution. All concentrations are expressed in mg/mL.

The acetyl and succinoyl content of the polymers are determined by the following formulae:

$$\text{Acetyl(wt \%)} = 100 \times \frac{43.04}{60.05} \times \frac{\left([\text{Acetic Acid}]_{Hyd} - [\text{Acetic Acid}]_{free} \times \frac{[\text{Polymer}]_{Hyd}}{[\text{Polymer}]_{free}}\right)(\text{mg/mL})}{[\text{Polymer}]_{Hyd}(\text{mg/mL})},$$

and $$\text{Succinoyl (wt \%)} = 100 \times \frac{101.08}{118.09} \times \frac{\left([\text{Succinic Acid}]_{Hyd} - [\text{Succinic Acid}]_{free} \times \frac{[\text{Polymer}]_{Hyd}}{[\text{Polymer}]_{free}}\right)(\text{mg/mL})}{[\text{Polymer}]_{Hyd}(\text{mg/mL})},$$

where [Acetic Acid]$_{Hyd}$ and [Succinic Acid]$_{Hyd}$ are the concentrations of acetic and succinic acids in the hydrolyzed sample solution, respectively; [Acetic Acid]$_{free}$ and [Succinic Acid]$_{free}$ are the concentrations of free acetic and succinic acids in the non-hydrolyzed control solutions, respectively; and [Polymer]$_{free}$ and [Polymer]$_{Hyd}$ are the concentrations of the initially added polymer in the non-hydrolyzed control solution and in the hydrolyzed sample solution, respectively. All concentrations are expressed in mg/mL.

The above analyses give the weight percentages of methoxy, hydroxypropoxy, acetyl, and succinoyl groups on the polymer. This information is used to calculate the degree of substitution for each substituent on the polymer using the following procedure.

First, the weight percentage of the polymer that is the backbone (that is, the fraction of the polymer that is not methoxy, hydroxypropoxy, acetyl, or succinoyl groups) is determined by the following equation:

Backbone(wt %)=100−methoxy(wt %)−hydroxypropoxy(wt %)−acetyl(wt %)−succinoyl(wt %)

Next, the number of moles of backbone per 100 gm of polymer, $M_{backbone}$ is estimated from the following equation:

$$M_{backbone} = \frac{(\text{Backbone(wt \%)} + (\text{methoxy(wt \%)} + \text{hydroxypropoxy(wt \%)}) \times 16)}{159}$$

This equation accounts for the fact that the weight percents for methoxy and hydroxypropoxy groups include the oxygen that was part of the hydroxyl group on the saccharide repeat unit, while the weight percents for acetyl and succinoyl groups do not. One skilled in the art will realize that this equation is only an approximation; an iterative calculation is required to determine the actual number of moles of backbone per 100 gm of polymer. However, the inventors have found that this approximation generally results in a calculated degree of substitution that is within the error range for measurements of the weight percentages of substituents on the polymer, and greatly reduces the number of calculations required to determine the degree of substitution. As used herein, the degree of substitution is calculated using this approximation.

The degrees of substitution of the substituents ($DS_i$), where i represents the substituent) are then determined by dividing the number of moles of the substituent (calculated by dividing the weight percent of the substituent by the molecular weight of the substituent) by the number of moles of the backbone, as follows:

$$DS_M = \frac{\text{methoxy(wt \%)}/31.03}{M_{backbone}},$$

$$DS_{HP} = \frac{\text{hydroxypropoxy(wt \%)}/75.09}{M_{backbone}},$$

$$DS_{Ac} = \frac{\text{acetyl(wt \%)}/43.04}{M_{backbone}}, \text{ and}$$

$$DS_S = \frac{\text{succinoyl(wt \%)}/101.08}{M_{backbone}}.$$

IV. ACTIVE AGENTS

Compositions containing HPMCAS are suitable for use with a biologically active compound desired to be administered to a patient in need of the active agent. The compositions may contain one or more active agents. The compositions are particularly suitable for low-solubility active agents.

In one embodiment, the active agent is a small molecule. In another embodiment, the active agent is a biological active agent. In still another embodiment, the active agent is a mixture of a small molecule and a biological active agent.

Preferably, the active agent is a "low-solubility active agent," meaning that the active agent has a minimum aqueous solubility at physiologically relevant pH (e.g., pH 1-8) of 0.5 mg/mL or less. Some embodiments of the disclosed polymers find greater utility as the aqueous solubility of the active agent decreases. Thus, some disclosed embodiments of compositions containing HPMCAS polymers are preferred for low-solubility active agents having an aqueous solubility of less than 0.2 mg/mL, more preferred for low-solubility active agents having an aqueous solubility of less than 0.1 mg/mL, more preferred for low-solubility active agents having an aqueous solubility of less than 0.05 mg/mL, and even more preferred for low-solubility active agents having an aqueous solubility of less than 0.01 mg/mL. In general, it may be said that the active agent has a dose-to-aqueous solubility ratio greater than 10 mL, and more typically greater than 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

The active agent does not need to be a low-solubility active agent in order to benefit from the disclosed compositions, although low-solubility active agents represent a preferred class for use with some embodiments of the compositions. Even an active agent that nonetheless exhibits appreciable aqueous solubility in the desired environment of use can benefit from the enhanced aqueous concentration and improved bioavailability made possible by certain embodiments of the disclosed compositions if the composition reduces the size of the dose needed for therapeutic efficacy or increases the rate of active agent absorption in cases where a rapid onset of the active agent's effectiveness is desired. In such cases, the active agent may have an aqueous solubility up to 1 to 2 mg/mL, or even as high as 20 to 40 mg/mL.

Examples of classes of active agents include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, triglyceride-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

An active agent should be understood to include any pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrug agents.

V. PHARMACEUTICAL COMPOSITIONS

Embodiments of pharmaceutical compositions including a low-solubility active agent and an HPMCAS polymer are disclosed. The amount of the polymer relative to the amount of active agent present in the disclosed pharmaceutical compositions depends on the active agent and combination of substituent levels on the polymer and may vary widely from an active agent-to-polymer weight ratio of from 0.01 to 100 (e.g., 1 wt % active agent to 99 wt % active agent). In most cases it is preferred that the active agent-to-polymer ratio is greater than 0.05 (4.8 wt % active agent) and less than 20 (95 wt % active agent).

In a preferred embodiment, the composition has a high loading of active agent. By "high loading of active agent" is meant that the pharmaceutical composition comprises at least 40 wt % active agent. Preferably, the pharmaceutical composition comprises at least 45 wt % active agent, and more preferably at least 50 wt % active agent. Such high loadings of active agent are desirable to keep the mass of the pharmaceutical composition at a low value.

The active agent and the polymer may be combined in any suitable manner, including by blending or mixing (e.g., by wet or dry granulation), coating active agent particles partially or fully with the polymer, coating a tablet comprising the active agent with the polymer, co-administration (i.e., administering the two components separately, but within the same general timeframe). In a preferred embodiment, the active agent and polymer are combined to form a solid amorphous dispersion as described below.

VI. SOLID AMORPHOUS DISPERSIONS

In one embodiment, the composition is in the form of a solid dispersion comprising the active agent and the HPMCAS, wherein at least 90 wt % of the active agent in the dispersion is non-crystalline.

The relative amounts of active agent and HPMCAS in the dispersion may range from 0.01 wt % to 99 wt % active agent, and from 1 wt % to 99.99 wt % HPMCAS. In other embodiments, the amount of active agent may range from 0.1 wt % to 80 wt %, or from 0.1 to 60 wt %, or from 1 to 40 wt %. The amount of HPMCAS may range from 20 wt % to 99.9 wt %, 40 wt % to 99.9 wt % or from 60 wt % to 99 wt %. In still another embodiment, the dispersions have the following composition: from 0.1 to 80 wt % active agent, and from 20 to 99.9 wt % HPMCAS. In yet another embodiment, the dispersions have the following composition: from 0.1 to 60 wt % active agent, and from 40 to 99.9 wt % HPMCAS. In another embodiment, the dispersions have the following composition: from 1 to 40 wt % active agent, and from 60 to 99 wt % HPMCAS.

In one embodiment, at least 90 wt % of the active agent present in the dispersion is amorphous. By "amorphous" is meant that the active agent is non-crystalline as determined by differential scanning calorimetry, powder X-ray diffraction (PXRD), by solid state nuclear magnetic resonance (NMR), or by any other known quantitative measurement.

As the HPMCAS is amorphous, the dispersion may comprise one or more active agent-rich domains dispersed in a HPMCAS phase, or the dispersion may comprise a solid solution of active agent molecules dispersed in the HPMCAS, or the dispersions may comprise any state or combination of states in between. In one embodiment, the dispersions have at least one Tg due to the amorphous character of the polymer. In another embodiment, essentially all of the active agent and the HPMCAS in the dispersion are in the form of a solid solution. Thus, in one embodiment, the composition consists essentially of a solid solution of the active agent and the HPMCAS.

In another embodiment, the dispersion comprises two or more active agents.

In still another embodiment, the relative amounts of active agent and polymer are chosen so that the dispersions have a glass transition temperature of at least 50° C. at 50% relative humidity. In another embodiment, when evaluated at a relative humidity of less than 5%, the dispersions have a glass transition temperature of at least 50° C., or at least 80° C., or even at least 100° C. The solid dispersion has a single glass transition temperature, indicating that the solid dispersion is a homogeneous solid solution.

The solid dispersions of the present invention may be formed by any method known in the art, including milling, extrusion, precipitation, or solvent addition followed by solvent removal. For example, active agent and the HPMCAS may be processed by heat, mechanical mixing and extrusion using, for example, a twin-screw extruder. The product may then be milled to the desired particle size. In another example, the active agent and HPMCAS are dissolved in a solvent in which both materials are soluble. The dispersions may then be formed from the solution by any known process, including precipitation in a miscible non-solvent, emulsifying in an immiscible non-solvent, or by forming droplets followed by removal of the solvent by evaporation.

In one embodiment, the solid dispersion is formed by spray drying. The active agent, the HPMCAS, and optional excipients may be dissolved in a solvent. Thus, the fluid that is spray dried may be a suspension or a homogeneous solution or a combination of dissolved and suspended materials. In one embodiment, the fluid that is spray dried comprises a homogeneous solution of active agent and HPMCAS dissolved together in a solvent. In another embodiment, the fluid that is spray dried consists essentially of a solution of active agent and HPMCAS dissolved in a solvent. In still another embodiment, the fluid that is spray dried comprises a suspension of active agent particles in a solution of HPMCAS dissolved in a solvent.

The solvent may be any solvent or mixture of solvents capable of dissolving both the active agent and polymer having a boiling point of less than about 150° C. Suitable solvents include water, acetone, methanol, ethanol, methyl acetate, ethyl acetate, tetrahydrofuran (THF), dichloromethane and mixtures of solvents. When the spray drying solution comprises an organic solvent that is water miscible, such as acetone or methanol, water may be added to the solution. The spray drying solution is then sprayed through an atomizer such as a pressure nozzle or two fluid nozzle into a spray drying chamber. The droplets are contacted with a heated drying gas such as dry nitrogen. Droplets dry rapidly, forming particles of the solid amorphous dispersion comprising the active agent and HPMCAS. The particles exit the spray dryer and are collected, such as in a cyclone.

In one embodiment, the solid dispersion is formed in the presence of a high surface area substrate. Exemplary high surface area substrates include inorganic oxides, such as $SiO_2$ (fumed silica), $TiO_2$, $ZnO_2$, $ZnO$, $Al_2O_3$, zeolites, and inorganic molecular sieves; water insoluble polymers, such as cross-linked cellulose acetate phthalate, cross-linked hydroxypropyl methyl cellulose acetate succinate, cross-linked polyvinyl pyrrolidinone, (also known as cross povidone), cross-linked cellulose acetate phthalate, microcrystalline cellulose, polyethylene/polyvinyl alcohol copolymer, polyethylene polyvinyl pyrrolidone copolymer, cross-linked carboxymethyl cellulose, sodium starch glycolate, cross-linked polystyrene divinyl benzene; and activated carbons. In one embodiment, the substrate is fumed silica. In this embodiment, the solid dispersion may be adsorbed onto the surface of the substrate, coated on the outside of the substrate, or any combination of these.

In another embodiment, the solid dispersion may be formed as a coating on an appropriate substrate. For example, the solid dispersion may be coated onto multiparticulates having diameters ranging from 50 μm to 5,000 μm. In another example, the solid dispersion may be coated onto a tablet or capsule. In still another embodiment, the solid dispersion may be formed into a layer that is incorporated into a tablet.

VII. PHYSICAL STABILITY

Solid amorphous dispersions comprising a low-solubility active agent and an embodiment of the disclosed HPMCAS polymers generally have improved physical stability. As used herein, "physical stability" or "physically stable" means either (1) the tendency of the amorphous active agent present in the dispersion to crystallize or (2) when the dispersion is substantially homogeneous, the tendency of the active agent to separate into active agent-rich domains—the active agent in the active agent-rich domains being amorphous or crystalline. Thus, a dispersion that is more physically stable than another will have either (1) a slower rate of active agent crystallization in the dispersion, or (2) a slower rate of formation of active agent-rich domains. Specifically, in certain embodiments, the solid amorphous dispersions have sufficient stability that less than 10 wt % of the active agent in the dispersion crystallizes during storage for 3 weeks at 25° C. and 10% RH. Preferably, less than 5 wt % of the active agent crystallizes during storage for 3 weeks at 25° C. and 10% RH.

In one embodiment, a solid amorphous dispersion made using a low-solubility active agent and an HPMCAS polymer, as disclosed herein, provides improved physical stability relative to a control composition. The control composition used to evaluate physical stability consists essentially of a solid amorphous dispersion of an equivalent amount of active agent in an equivalent amount of HPMCAS, but wherein the HPMCAS is a commercial grade of HPMCAS (e.g., either the AQOAT "L" grade, "M" grade, or "H" grade). In particular, physical stability may be evaluated by comparing the rate of crystallization of the drug in a test composition with the rate in a control composition, by comparing the rate of phase separation of the drug in a test composition with the rate in a control composition, or by comparing the rate of phase separation of drug from the drug/polymer dispersion of the test composition with the rate in a control composition, as described in U.S. Published Patent Application No. 2008/0262107, which is incorporated herein by reference.

The improvement in physical stability for compositions including the disclosed HPMCAS polymers allows formation of solid amorphous dispersions with a higher active agent loading (e.g., higher active agent:polymer ratio) while still retaining good physical stability.

VIII. CONCENTRATION ENHANCEMENT

In another separate embodiment, compositions containing the HPMCAS polymers are concentration enhancing. The term "concentration enhancing" means that the polymer is present in a sufficient amount in the composition so as to improve, or increase, the concentration of dissolved active agent in an aqueous use environment relative to a control composition free from the polymer. As used herein, a "use environment" can be either the in vivo environment of the gastrointestinal tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS), simulated intestinal buffer without enzymes (SIN), a Model Fasted Duodenal (MFD) solution, or a solution to model the fed state. Concentration enhancement may be determined through either in vitro dissolution tests or through in vivo tests. It has been determined that enhanced active agent concentrations in in vitro dissolution tests in such in vitro test solutions provide good indicators of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate SIN solution is 50 mM $KH_2PO_4$ adjusted to pH 7.4. An appropriate MFD solution is the same PBS solution wherein additionally is present 7.3 mM sodium taurocholic acid and 1.4 mM of 1-palmitoyl-2-oleyl-sn-glycero-3-phosphocholine. An appropriate solution to model the fed state is the same PBS solution wherein additionally is present 29.2 mM sodium taurocholic acid and 5.6 mM of 1-palmitoyl-2-oleyl-sn-glycero-3-phosphocholine. In particular, a composition may be dissolution-tested by adding it to an in vitro test solution and agitating to promote dissolution, or by performing a membrane-permeation test as described in U.S. Published Patent Application No. 2008/0262107, which is incorporated herein by reference.

In one aspect, an embodiment of a composition including an HPMCAS polymer, when dosed to an aqueous use environment, provides a maximum active agent concentration (MAAC) that is at least 1.25-fold the MAAC provided by a control composition that does not include the polymer. In other words, if the MAAC provided by the control composition is 100 μg/mL, then a composition containing a concentration-enhancing polymer provides an MAAC of at least 125 μg/mL. More preferably, the MAAC of active agent achieved with compositions including the disclosed HPMCAS polymers are at least 2-fold, even more preferably at least 3-fold, and most preferably at least 5-fold that of the control composition. Surprisingly, the compositions may achieve extremely large enhancements in aqueous concentration. In some cases, the MAAC of very hydrophobic active agents provided by compositions including the disclosed HPMCAS polymers are at least 10-fold, at least 50-fold, at least 200-fold, at least 500-fold, to more than 1000-fold that of the control composition.

The control composition is conventionally the undispersed active agent alone (e.g., typically, the crystalline active agent alone in its most thermodynamically stable crystalline form, or in cases where a crystalline form of the active agent is unknown, the control may be the amorphous active agent alone) or the active agent plus a weight of inert diluent equivalent to the weight of polymer in the test composition. By inert is meant that the diluent is not concentration enhancing. Thus, the control composition includes the active agent, but does not include the HPMCAS polymer.

Alternatively, some embodiments of compositions including the disclosed HPMCAS polymers provide in an aqueous use environment a concentration versus time Area Under the Curve (AUC), for any period of at least 90 minutes between the time of introduction into the use environment and 270 minutes following introduction to the use environment that is at least 1.25-fold that of the control composition. More preferably, the AUC in the aqueous use environment achieved with certain embodiments of the disclosed compositions are at least 2-fold, more preferably at least 3-fold, and most preferably at least 5-fold that of a control composition. For some hydrophobic active agents, the compositions may provide an AUC value that is at least 10-fold, at least 25-fold, at least 100-fold, and even more than 250-fold that of the control described above.

Alternatively, some embodiments of compositions containing the disclosed HPMCAS polymers, when dosed orally to a human or other animal, provide an AUC in active agent concentration in the blood plasma or serum that is at least 1.25-fold that observed when an appropriate control composition (i.e., a composition including the active agent without the HPMCAS polymer) is dosed. Preferably, the blood AUC is at least 2-fold, preferably at least 3-fold, preferably at least 4-fold, preferably at least 6-fold, preferably at least 10-fold, and even more preferably at least 20-fold that of the control composition. It is noted that such compositions can also be said to have a relative bioavailability of from 1.25-fold to 20-fold that of the control composition. Thus, certain embodiments of the disclosed compositions, when evaluated, meet either the in vitro or the in vivo, or both, performance criteria.

Alternatively, some embodiments of compositions including the disclosed HPMCAS polymers, when dosed orally to a human or other animal, provide maximum active agent concentration in the blood plasma or serum ($C_{max}$) that is at least 1.25-fold that observed when an appropriate control composition is dosed. Preferably, the blood $C_{max}$ is at least 2-fold, preferably at least 3-fold, preferably at least 4-fold, preferably at least 6-fold, preferably at least 10-fold, and even more preferably at least 20-fold that of the control composition.

Alternatively, the disclosed compositions, when dosed orally to a human or other animal, may result in improved bioavailability or $C_{max}$. Relative bioavailability and $C_{max}$ of active agents in the compositions can be tested in vivo in animals or humans using conventional methods for making such a determination. An in vivo test, such as a crossover study, may be used to determine whether a composition of active agent and polymer provides an enhanced relative bioavailability or $C_{max}$ compared with a control composition as described above. In an in vivo crossover study, a test composition comprising a low-solubility active agent and polymer is dosed to half a group of test subjects and, after an appropriate washout period (e.g., one week) the same subjects are dosed with a control composition that consists of an equivalent quantity of crystalline active agent as the test composition (but with no polymer present). The other half of the group is dosed with the control composition first, followed by the test composition. The relative bioavailability is measured as the concentration of active agent in the blood (serum or plasma) versus time area under the curve determined for the test group divided by the AUC in the blood provided by the control composition. Preferably, this test/control ratio is determined for each subject, and then the ratios are averaged over all subjects in the study. In vivo determinations of AUC and $C_{max}$ can be made by plotting the serum or plasma concentration of active agent along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the aqueous solubility of the active agent in vivo. The determination of AUCs and $C_{max}$ is a well-known procedure and is described, for example, in Welling, "Pharmacokinetics Processes and Mathematics," *ACS Monograph* 185 (1986).

IX. EXCIPIENTS AND DOSAGE FORMS

The inclusion of other excipients in the composition may be useful in order to formulate the composition into tablets, capsules, suspensions, powders for suspension, creams, transdermal patches, depots, and the like. The composition of active agent and polymer can be added to other dosage form ingredients in essentially any manner that does not substantially alter the active agent. When the disclosed composition is in the form of a solid amorphous dispersion, the excipients may be either physically mixed with the dispersion and/or included within the dispersion.

Conventional formulation excipients may be employed in embodiments of the disclosed compositions, including those excipients well-known in the art (e.g., as described in *Remington: The Science and Practice of Pharmacy* (20$^{th}$ ed., 2000). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the active agent/polymer composition has been formed, in order to formulate the composition into tablets, capsules, suppositories, suspensions, powders for suspension, creams, transdermal patches, depots, and the like.

Embodiments of the disclosed compositions may be delivered by a wide variety of routes, including, but not limited to, oral, nasal, rectal, vaginal, subcutaneous, intravenous and pulmonary. Generally, the oral route is preferred.

Other features and embodiments of the disclosed HPMCAS polymers and compositions including the polymers will become apparent from the following examples that are given for illustration rather than for limiting the intended scope of the disclosed embodiments.

X. EXAMPLES

Example 1

Synthesis and Characterization of HPMCAS Polymers

Polymers 1-3 were synthesized, and were designated HPMCAS-K(1), HPMCAS-K(2), and HPMCAS-K(3), respectively. The K designation refers to the starting material (hydroxypropyl methyl cellulose) grade, i.e., METHOCEL® K3 Premium LV (Dow Chemical). K-grade METHOCEL® has a methoxyl content of 19-24% by weight. In comparison, E-grade METHOCEL® has a methoxyl content of 28-30% by weight. The 1, 2, and 3 designations refer to low, medium, and high ratios of acetate to succinate substitution.

1. HPMCAS-K(1): 122 g HPMC (Dow METHOCEL® K3 Premium LV) was combined with 198.8 g glacial acetic acid in a glass reaction vessel equipped with a condenser and a nitrogen purge, and heated to 91° C. with stirring at 450 rpm. Next, 97.9 g of acetic anhydride were added slowly over several minutes. A dry mix of 20.5 g succinic anhydride, 39.5 g sodium acetate, and 1.9 g sodium chlorate was added and allowed to react with stirring for one hour. A second dry mix of 20.6 g succinic anhydride and 39.8 g sodium acetate was added and allowed to react with stirring for 3.5 hours. The reaction was then quenched by adding the reaction mixture to water. The polymer was collected by filtration, and washed several times with water. The polymer was then dried prior to use.

2. HPMCAS-K(2): 122 g HPMC (Dow METHOCEL® K3 Premium LV) was combined with 165 g glacial acetic acid and heated to 91° C. for 1.75 hours with stirring at 450 rpm using the same apparatus as described above. Next, 109.5 g acetic anhydride was added slowly over several minutes. A dry mix of 15 g succinic anhydride, 36.2 g sodium acetate, and 1.8 g sodium chlorate was added and allowed to react with stirring for 5 minutes. A second dry mix of 36.2 g sodium acetate and 15 g succinic anhydride was added and allowed to react with stirring for 6 hours. The reaction was then quenched and purified as described above.

3. HPMCAS-K(3): 122.2 g HPMC (Dow METHOCEL® K3 Premium LV) was combined with 121 g glacial acetic acid and heated to 91° C. with stirring at 50 rpm. Additional acetic acid was added to reduce the solids content to 40 wt %. Next, 142 g acetic anhydride was added, followed by a dry mix of 8 g succinic anhydride, 38.5 g sodium acetate, and 1.9 g sodium chlorate was added and allowed to react with stirring at 450 rpm for 45 minutes. Stirring was reduced to 200 rpm, and the reaction proceeded for an additional 15 minutes. Stirring was increased to 330 rpm, and a second dry mix of 38.5 g sodium acetate and 8 g succinic anhydride was added. The flask was opened to the atmosphere for 30 minutes to evaporate excess acetic acid. The flask was then closed and allowed to reflux with stirring at 250 rpm for 6.5 hours. The reaction was then quenched and purified as described above.

Characterization

The degrees of substitution of acetate and succinate in each polymer were determined as described above in section III. The apparent molecular weights were determined by size exclusion chromatography. The results are shown in Table 3 and in FIG. 1. For comparison, the degrees of substitution and molecular weights of commercially available HPMCAS polymers (from Shin-Etsu) are also shown. The Shin-Etsu molecular weights are historical ranges.

TABLE 3

| No. | Polymer | Apparent Mol. Wt. (Daltons) | DS Acetate | DS Succinate | Acetate/ Succinate Ratio |
|---|---|---|---|---|---|
| 1 | HPMCAS-K(1) | 522K | 0.85 | 0.68 | 1.3 |
| 2 | HPMCAS-K(2) | 605K | 1.15 | 0.48 | 2.4 |
| 3 | HPMCAS-K(3) | 386K | 1.41 | 0.25 | 5.6 |
|   | HPMCAS-L (Shin-Etsu) | 80-130K | 0.47 | 0.40 | 1.2 |
|   | HPMCAS-M (Shin-Etsu) | 100-120K | 0.55 | 0.28 | 2.0 |
|   | HPMCAS-H (Shin-Etsu) | 100-400K | 0.65 | 0.16 | 4.1 |

Figure 2:
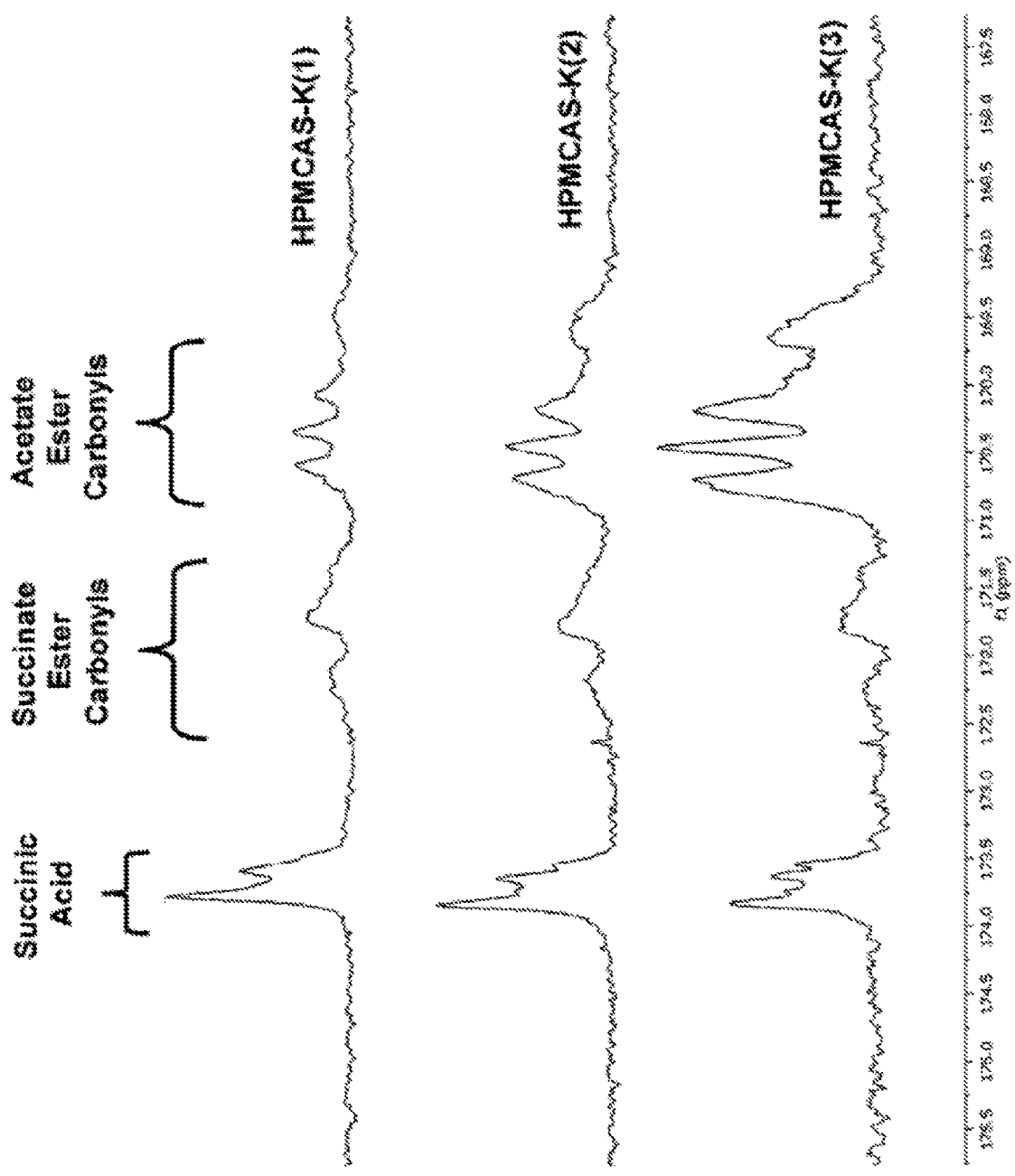
FIG. 2 shows $^{13}C$ NMR spectra of several embodiments of the HPMCAS polymers.

Substitution by acetyl and succinoyl groups can occur on available C2, C3 or C6 carbons within the saccharide ring, or on the distal end of the hydroxypropoxy (HP) groups. To determine the regiochemistry of the substitutions, $^{13}$C NMR was performed with the results shown in Table 4 for the degrees of substitution at each available site. FIG. 2 shows the NMR spectra of HPMCAS-K(1), HPMCAS-K(2), and HPMCAS-K(3).

TABLE 4

| | Succinate | | | | Acetate | | | |
|---|---|---|---|---|---|---|---|---|
| Polymer | C6 | HP | C3 | C2 | C6 | HP | C3 | C2 |
| 1 | 0.17 | 0 | 0.32 | 0.19 | 0.27 | 0.27 | 0.19 | 0.12 |
| 2 | 0.13 | 0 | 0.21 | 0.14 | 0.35 | 0.37 | 0.27 | 0.16 |
| 3 | 0.03 | 0 | 0.11 | 0.08 | 0.36 | 0.43 | 0.37 | 0.25 |

Figure 3:
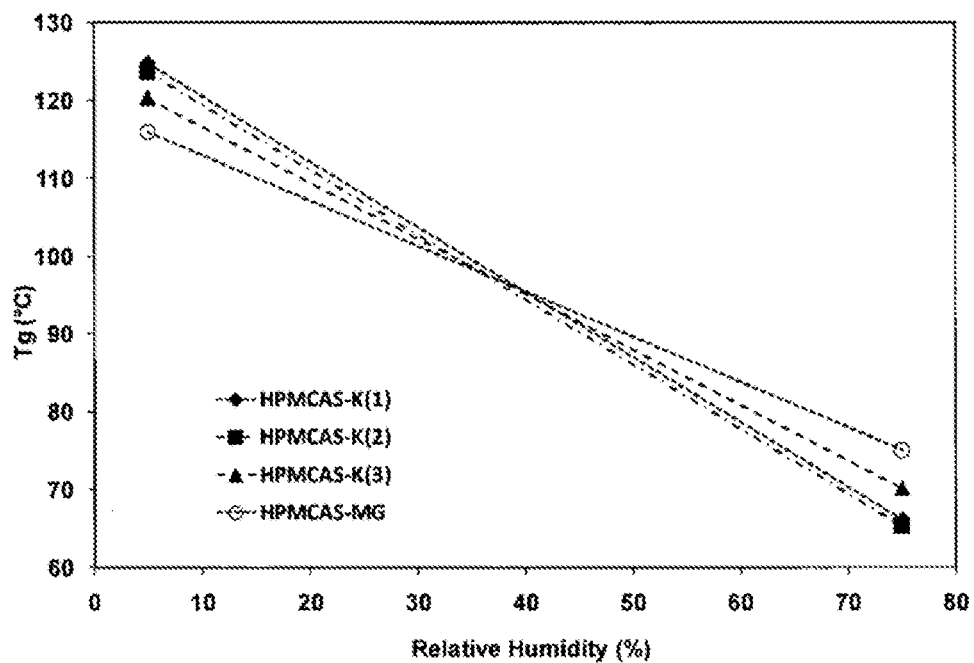
FIG. 3 is a graph of glass transition temperature versus percent relative humidity for several embodiments of HPMCAS polymers.

The glass transition temperature of a polymer is related to its physical stability. Typically physical stability is greater for polymers with high $T_g$ values. The glass transition temperatures of the synthesized polymers were measured at 75% relative humidity (RH) and less than 5% RH. For comparison, the glass transition temperature of E-grade HPMCAS-MG was determined. As shown in Table 5, the synthesized polymers have glass transition temperatures that were similar to HPMCAS-MG. FIG. 3 is a graph of glass transition temperature versus percent relative humidity for the evaluated polymers.

TABLE 5

| Polymer | $T_g$ (° C.) at <5% RH | $T_g$ (° C.) at 75% RH |
|---|---|---|
| HPMCAS-K(1) | 125 | 66 |
| HPMCAS-K(2) | 124 | 65 |
| HPMCAS-K(3) | 120 | 70 |
| HPMCAS-MG | 116 | 75 |

Figure 4:
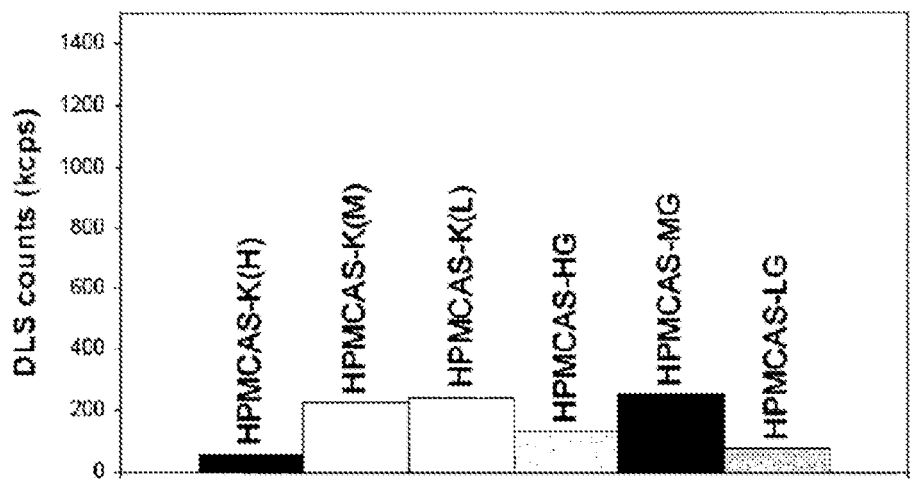
FIG. 4 is a bar graph illustrating the turbidity of several embodiments of HPMCAS polymers at pH 5.5.
Figure 5:
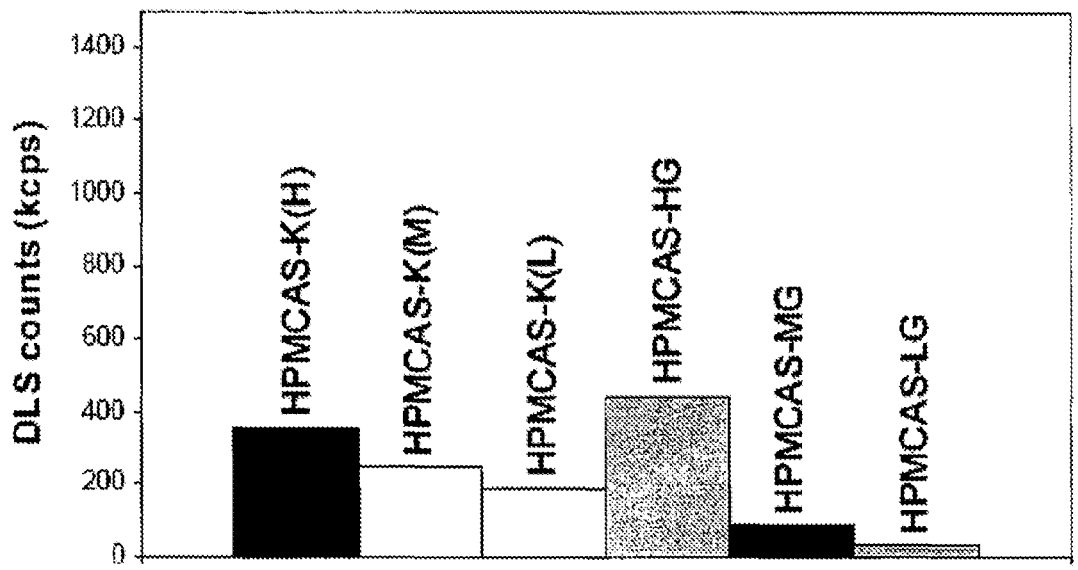
FIG. 5 is a bar graph illustrating the turbidity of several embodiments of HPMCAS polymers at pH 6.5.
Figure 6:
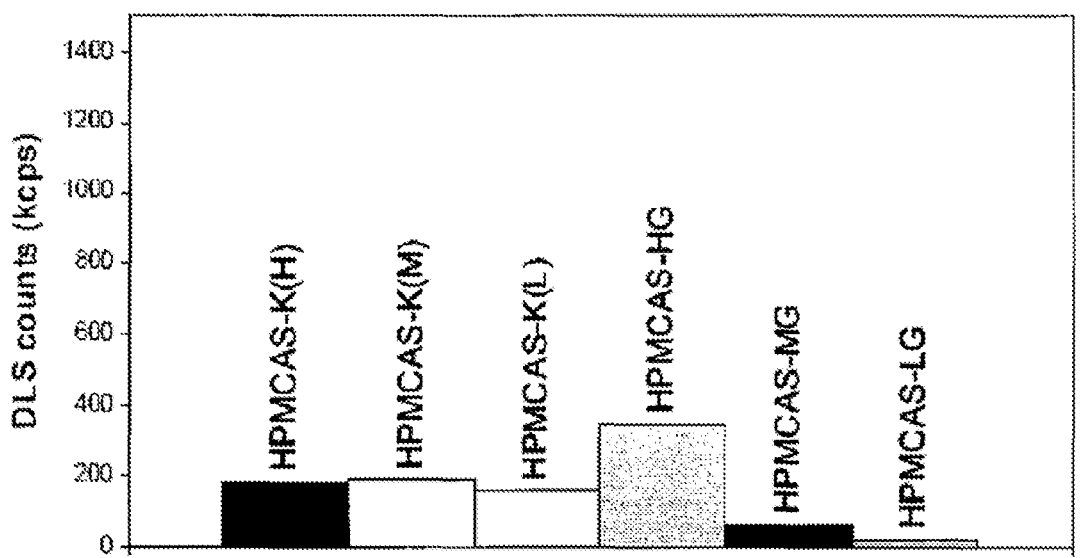
FIG. 6 is a bar graph illustrating the turbidity of several embodiments of HPMCAS polymers at pH 7.5.

The colloidal nature of the disclosed polymers of this Example was evaluated and compared to the colloidal nature of HPMCAS polymers synthesized from E-grade HPMC with low, medium, or high ratios of acetate/succinate substitution (HPMCAS-LG, -MG, and -HG). For each polymer, 10 mL of a 1.0 wt % solution in PBS buffer was prepared and adjusted to pH 5.5, 6.5, or 7.5. The samples were stirred at 37° C. for 3 hours. The pH was checked and adjusted as necessary using dilute sodium hydroxide. The samples were stirred at 37° C., 700 rpm for an additional 21 hours. Insoluble polymer was removed by filtering each sample through a 1.0 μm glass filter. Colloidal and dissolved polymer passed through the 1.0 μm glass filter. Turbidity measurements were performed using dynamic light scattering (DLS) on a ZetaPALS instrument (Brookhaven Instruments). Light intensity was maximized using the HPMCAS-MG sample at pH 5.5. Colloid diameter was determined by DLS BI-200SM particle size analyzer with a BI-9000AT correlator. The sums of exponentials from the autocorrelation functions were analyzed using CONTIN software to extract size distributions from the samples. At pH 5.5 (Table 6, FIG. 4), HPMCAS-K(2) and HPMCAS-K(1) showed about the same amount of colloidal species as the E-grade HPMCAS-MG. HPMCAS-K(3) had the lowest turbidity value. At pH 6.5 (Table 7, FIG. 5), all three K-grade HPMCAS polymers exhibited greater amounts of colloidal species than the E-grade MG and LG polymers. However, the E-grade HG polymer was the most turbid at pH 6.5. At pH 7.5 (Table 8, FIG. 6), all three K-grade HPMCAS polymers formed roughly the same amount of colloidal species, which was greater than the E-grade MG and LG polymers. The E-grade HG polymer exhibited the greatest turbidity at pH 7.5.

TABLE 6 pH 5.5 (24 hr.)

| Polymer | Counts (kcps) | Diameter (nm) |
|---|---|---|
| HPMCAS-K(3) | 58 | 420 |
| HPMCAS-K(2) | 225 | 363 |
| HPMCAS-K(1) | 242 | 444 |
| HPMCAS-HG | 131 | 309 |
| HPMCAS-MG | 252 | 526 |
| HPMCAS-LG | 74 | — |

TABLE 7 pH 6.5 (24 hr.)

| Polymer | Counts (kcps) | Diameter (nm) |
|---|---|---|
| HPMCAS-K(3) | 357 | 548 |
| HPMCAS-K(2) | 245 | 339 |
| HPMCAS-K(1) | 192 | 447 |
| HPMCAS-HG | 446 | 476 |
| HPMCAS-MG | 89 | — |
| HPMCAS-LG | 29 | — |

TABLE 8 pH 7.5 (24 hr.)

| Polymer | Counts (kcps) | Diameter (nm) |
|---|---|---|
| HPMCAS-K(3) | 181 | 270 |
| HPMCAS-K(2) | 192 | 298 |
| HPMCAS-K(1) | 158 | 408 |
| HPMCAS-HG | 350 | 437 |
| HPMCAS-MG | 66 | — |
| HPMCAS-LG | 25 | — |

Example 2

Phenyloin Precipitation Inhibition and In Vitro Concentration Enhancement

Figure 7:
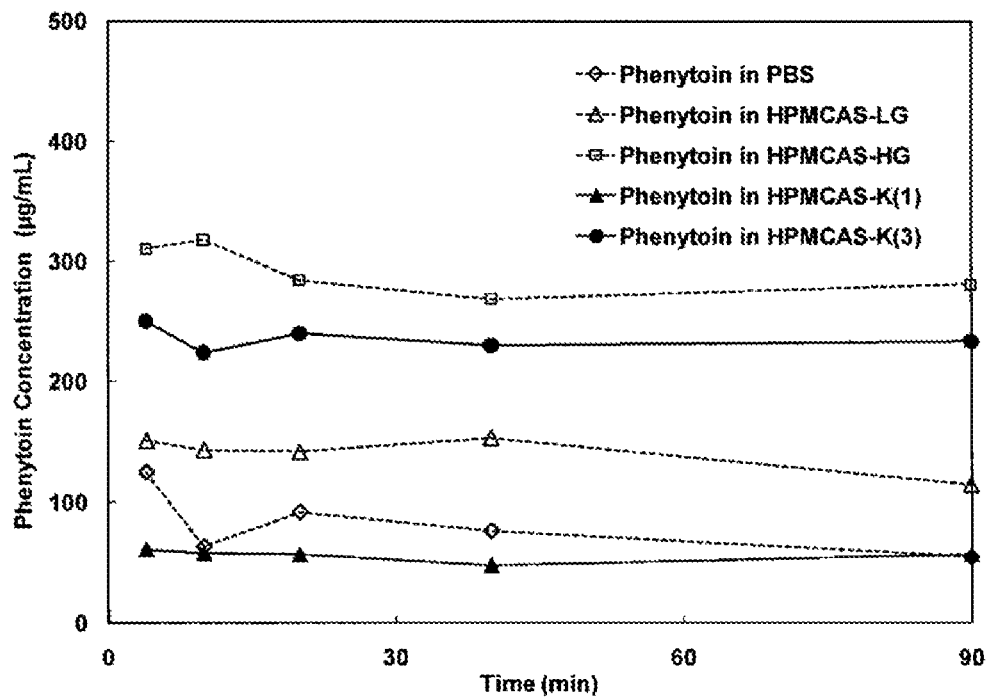
FIG. 7 is a graph of concentration versus time for phenyloin dissolution in solutions containing embodiments of HPMCAS polymers.

The dissolution properties of phenyloin in HPMCAS-K(3) and HPMCAS-K(1) were measured and compared to the dissolution of phenyloin in E-grade HPMCAS-HG and HPMCAS-LG. Phenyloin was dissolved in methanol at a concentration of 18 mg/mL. The polymers were dissolved in PBS (20 mM sodium phosphate ($Na_2HPO_4$), 47 mM potassium phosphate ($KH_2PO_4$), 87 mM NaCl, and 0.2 mM KCl, adjusted to pH 6.5 with NaOH) at a concentration of 1.5 mg/mL. Phenyloin dissolved in methanol was added to either PBS or a solution of PBS containing dissolved polymer at 37° C., such that the concentration of phenyloin would have been 500 µg/mL if all the phenyloin had dissolved. The dissolved concentrations of phenyloin in the polymer/PBS solutions were then measured by HPLC at 0, 5, 10, 20, 40, 90, and 1200 minutes. HPLC was performed using a ZORBAX® RX-C18 column (4.6×75 mm, 3.5 µm, Agilent Technologies) and a mobile phase comprising 0.2% $H_3PO_4$ in water, at a flow rate of 1.0 mL/min; 10 µL of each solution was injected. For each solution, the maximum concentration over the measured time-points in the first 90 minutes ($C_{max90}$) and the concentration at 1200 minutes ($C_{1200}$) after addition of the phenyloin were determined, along with the area under the curve from 0-90 minutes ($AUC_{90}$). As shown in Table 9 and FIG. 7, HPMCAS-K(3) inhibited phenyloin precipitation much better than HPMCAS-LG and PBS alone. HPMCAS-K(3) and HPMCAS-LG have similar degrees of succinate substitution (0.25 and 0.40, respectively (see Table 7)), but greatly different degrees of acetate substitution (1.41 and 0.47, respectively). Thus, the data indicate that increased acetate substitution increases inhibition of phenyloin precipitation.

TABLE 9

| Sample | $C_{max90}$ (µg/mL) | $AUC_{90}$ (min * µg/mL) | $C_{1200}$ (µg/mL) |
|---|---|---|---|
| Phenytoin in PBS | 120 | 6,500 | 80 |
| Phenytoin in HPMCAS-HG | 320 | 24,800 | 190 |
| Phenytoin in HPMCAS-LG | 150 | 12,300 | 100 |
| Phenytoin in HPMCAS-K(3) | 250 | 20,500 | 220 |
| Phenytoin in HPMCAS-K(1) | 60 | 4,700 | 50 |

Figure 8:
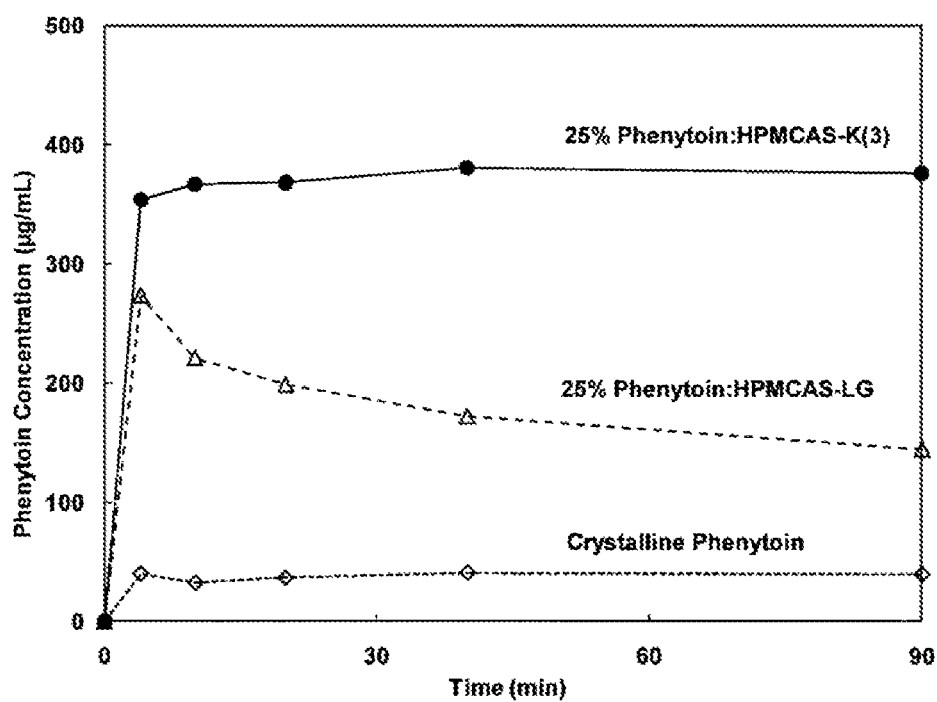
FIG. 8 is a graph of concentration versus time for dissolution of spray-dried dispersions containing phenyloin and embodiments of HPMCAS polymers in MFDS at pH 6.5.

Spray-dried dispersions (SDDs) comprising 25 wt % phenyloin in HPMCAS-K(3), HPMCAS-K(1), HPMCAS-HG, and HPMCAS-LG were prepared as described in section VIII. The SDDs and bulk phenyloin were evaluated in duplicate by microcentrifuge dissolution at 37° C. in MFDS, as described above in section X, to determine whether concentration enhancement was seen with the SDDs. Dissolved concentrations were measured by HPLC. As shown in Table 10 and FIG. 8, the phenyloin:HPMCAS-K(3) SDD exhibited better dissolution and sustainment than the phenyloin:HPMCAS-LG SDD or bulk phenyloin. The results indicate that increased acetate substitution relative to succinate substitution enhances dissolution of phenyloin.

TABLE 10

| Sample | $C_{max90}$ (µg/mL) | $AUC_{90}$ (min * µg/mL) | $C_{1200}$ (µg/mL) |
|---|---|---|---|
| Phenytoin bulk | 40 | 3,500 | 40 |
| 25% Phenytoin:HPMCAS-HG, 2 trials | 420 | 35,200 | 180 |
| 25% Phenytoin:HPMCAS-LG, 2 trials | 270 | 15,700 | 120 |

TABLE 10-continued

| Sample | $C_{max90}$ (µg/mL) | $AUC_{90}$ (min * µg/mL) | $C_{1200}$ (µg/mL) |
|---|---|---|---|
| 25% Phenytoin:HPMCAS-K(3), 2 trials | 380 | 32,900 | 210 |
| 25% Phenytoin:HPMCAS-K(1), 2 trials | 220 | 14,600 | 120 |

Example 3

Itraconazole Precipitation Inhibition and In Vitro Concentration Enhancement The dissolution properties of itraconazole in HPMCAS-K(3) and HPMCAS-K(1) were measured and compared to the dissolution of itraconazole in E-grade HPMCAS-HG and HPMCAS-LG (AQOAT-HG and AQOAT-LG, Shin Etsu). Itraconazole was dissolved in dimethyl sulfoxide (DMSO) at a concentration of 18 mg/mL. The polymers were dissolved in PBS (20 mM sodium phosphate ($Na_2HPO_4$), 47 mM potassium phosphate ($KH_2PO_4$), 87 mM NaCl, and 0.2 mM KCl, adjusted to pH 6.5 with NaOH) at a concentration of 1.5 mg/mL. Itraconazole dissolved in DMSO was added to either PBS or a solution of PBS and dissolved polymer at 37° C., such that the concentration of itraconazole would have been 500 µg/mL if all the itraconazole had dissolved. The dissolved concentrations of itraconazole in the solutions were then measured by HPLC at 0, 5, 10, 20, 40, 90, and 1200 minutes. HPLC was performed using a ZORBAX® RX-C18 column (4.6×75 mm, 3.5 µm, Agilent Technologies) and a mobile phase comprising 40% 10 mM ammonium acetate/60% acetonitrile, at a flow rate of 1.0 mL/min; 10 µL of each solution was injected. For each solution, the maximum concentration over the measured time-points in the first 90 minutes ($C_{max90}$) and the concentration at 1200 minutes ($C_{1200}$) after addition of the itraconazole were determined, along with the area under the curve from 0-90 minutes ($AUC_{90}$). As shown in Table 11, based upon $AUC_{90}$, HPMCAS-K(3) inhibited itraconazole precipitation much better than the other polymers or PBS alone. HPMCAS-K(1) exhibited similar precipitation inhibition to HPMCAS-HG and HPMCAS-LG. HPMCAS-K(3) has a much larger degree of acetate substitution (1.41) than HPMCAS-K(1) (0.85), HPMCAS-HG (0.65) and HPMCAS-LG (0.47), indicating that increased acetate substitution increases inhibition of itraconazole precipitation.

TABLE 11

| Sample | $C_{max90}$ (µg/mL) | $AUC_{90}$ (min * µg/mL) | $C_{1200}$ (µg/mL) | Theor $C_{max}$ (µg/mL) |
|---|---|---|---|---|
| Itraconazole in PBS | 110 | 3,600 | 60 | 500 |
| Itraconazole in HPMCAS-HG | 110 | 7,000 | 100 | 500 |
| Itraconazole in HPMCAS-LG | 190 | 7,700 | 20 | 500 |
| Itraconazole in HPMCAS-K(3) | 150 | 10,800 | 130 | 500 |
| Itraconazole in HPMCAS-K(1) | 170 | 7,900 | 20 | 500 |

Figure 9:
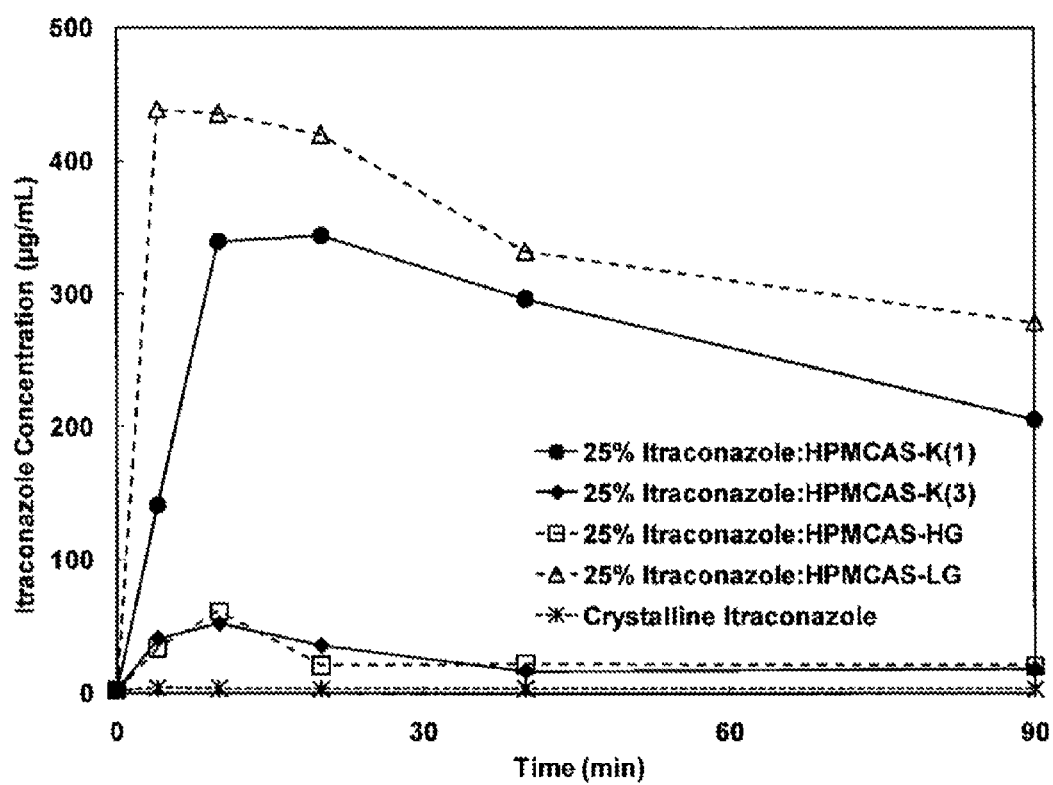
FIG. 9 is a graph of concentration versus time for dissolution of spray-dried dispersions containing itraconazole and embodiments of HPMCAS polymers in MFDS at pH 6.5.

Spray-dried dispersions (SDDs) comprising 25 wt % itraconazole in HPMCAS-K(1) and HPMCAS-HG were prepared as described in section VIII. The SDDs and bulk itraconazole were evaluated by microcentrifuge dissolution at 37° C. in MFDS, as described above in section X, to determine whether concentration enhancement was seen with the SDDs. Dissolved concentrations were measured by HPLC as described above. As shown in Table 12 and FIG. 9, the itraconazole:HPMCAS-K(1) SDD exhibited much better dissolution than the itraconazole:HPMCAS-HG SDD, the itraconazole:HPMCAS-K(3) SDD, or bulk itraconazole.

TABLE 12

| Sample | $C_{max90}$ (μg/mL) | $AUC_{90}$ (min * μg/mL) | $C_{1200}$ (μg/mL) |
|---|---|---|---|
| Itraconazole bulk | 0 | 300 | 0 |
| 25% Itraconazole:HPMCAS-HG, 2 trials | 60 | 2,200 | 20 |
| 25% Itraconazole:HPMCAS-LG, 2 trials | 440 | 30,600 | 60 |
| 25% Itraconazole:HPMCAS-K(3), 2 trials | 50 | 2,200 | 20 |
| 25% Itraconazole:HPMCAS-K(1), 2 trials | 340 | 24,100 | 60 |

In one embodiment a composition comprises an active agent; and hydroxypropyl methyl cellulose acetate succinate (HPMCAS) having a degree of substitution of methoxy groups ($DS_M$) of ≤1.45, and a combined degree of substitution of acetyl groups ($DS_{Ac}$) and succinoyl groups ($DS_S$) of ($DS_{Ac}+DS_S$)≥1.25. In other embodiments, any one or more of the above-relevant compositions may comprise ($DS_{Ac}+DS_S$)≥ 1.35. In other embodiments, any one or more of the above-relevant compositions may comprise 1.25≤($DS_{Ac}+DS_S$)≤1.9. In other embodiments, any one or more of the above-relevant compositions may comprise 1.5≤($DS_{Ac}+DS_S$)≤ 1.7. In other embodiments, any one or more of the above-relevant compositions may comprise $DS_{Ac}$≥0.5, $DS_S$≥0.20, and 1.25≤($DS_{Ac}+DS_S$)≤1.9.

In other embodiments, any one or more of the disclosed compositions may have a ratio of acetyl groups to succinoyl groups between 0.8 and 6.5. In other embodiments, any one or more of the disclosed compositions may have a ratio of acetyl groups to succinoyl groups between 1.0 and 6.0. In other embodiments, any one or more of the disclosed compositions may have a ratio of acetyl groups to succinoyl groups between 1.2 and 5.6.

In other embodiments, any one or more of the disclosed compositions may comprise 1.0≤$DS_{Ac}$≤1.5, and 0.20≤$DS_S$≤0.7.

In another embodiment the composition comprises an active agent; and hydroxypropyl methyl cellulose acetate succinate (HPMCAS) having a degree of substitution of methoxy groups ($DS_M$) of ≤1.45, a degree of substitution of acetyl groups ($DS_{Ac}$) of ≥0.5, and a degree of substitution of succinoyl groups ($DS_S$) of ≥0.20.

In another embodiment the composition comprises an active agent; and hydroxypropyl methyl cellulose acetate succinate (HPMCAS) having a degree of substitution of methoxy groups ($DS_M$) of ≤1.45, a combined degree of substitution of acetyl groups ($DS_{Ac}$) and succinoyl groups of ($DS_S$) of ($DS_{Ac}+DS_S$)≥1.25, a degree of substitution of acetyl groups ($DS_{Ac}$) of ≤1.2, and a degree of substitution of succinoyl groups ($DS_S$) of ≤0.9.

In other embodiments, any one or more of the disclosed compositions may be in the form of a solid amorphous dispersion wherein at least 90 wt % of said active agent in said dispersion is non-crystalline.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A composition comprising:
an active agent; and
hydroxypropyl methyl cellulose acetate succinate (HPMCAS) having a degree of substitution of methoxy groups ($DS_M$) of ≤1.45, a degree of substitution of acetyl groups ($DS_{Ac}$) of from 1.0 to 1.5, and a combined degree of substitution of acetyl groups ($DS_{Ac}$) and succinoyl groups ($DS_S$) of ($DS_{Ac}+DS_S$)≥1.25.
2. The composition of claim 1 wherein ($DS_{Ac}+DS_S$) 1.35.
3. The composition of claim 1, wherein 1.25≤($DS_{Ac}+DS_S$)≤ 1.9.
4. The composition of claim 1, wherein 1.5≤($DS_{Ac}+DS_S$)≤ 1.7.
5. The composition of claim 1, wherein:
$DS_{Ac}$ is from 1.0 to 1.5,
$DS_S$≥0.20, and
1.25≤($DS_{Ac}+DS_S$)≤1.9.
6. The composition of claim 1, wherein a ratio of acetyl groups to succinoyl groups is between 0.8 and 6.5.
7. The composition of claim 1 wherein the ratio of acetyl groups to succinoyl groups is between 1.0 and 6.0.
8. The composition of claim 1 wherein the ratio of acetyl groups to succinoyl groups is between 1.2 and 5.6.
9. The composition of claim 8, wherein:
1.0≤$DS_{Ac}$≤1.5, and
0.20≤$DS_S$≤0.7.
10. A composition comprising:
an active agent; and
hydroxypropyl methyl cellulose acetate succinate (HPMCAS) having a degree of substitution of methoxy groups ($DS_M$) of ≤1.45, a degree of substitution of acetyl groups ($DS_{Ac}$) of from 1.0 to 1.5, and a degree of substitution of succinoyl groups ($DS_S$) of ≥0.20.
11. The composition of claim 1 wherein said composition is in the form of a solid amorphous dispersion.
12. The composition of claim 11 which contains from 1 to 60 weight percent active ingredient and from 40 to 99 weight percent HPMCAS.
13. The composition of claim 12 wherein at least 90 wt % of the active agent is amorphous.
14. The composition of claim 11 wherein the active ingredient is a low solubility active ingredient.
15. The composition of claim 11 wherein the active ingredient is hydrophobic.
16. The composition of claim 1 which contains from 1 to 60 weight percent active ingredient and from 40 to 99 weight percent HPMCAS.

* * * * *